US 11,077,270 B2

(12) United States Patent
Magin et al.

(10) Patent No.: US 11,077,270 B2
(45) Date of Patent: Aug. 3, 2021

(54) PATTERNS FOR FLOW CONTROL AND BIOADHESION CONTROL

(71) Applicants: Sharklet Technologies, Inc., Aurora, CO (US); University of Florida Research Foundation, Inc., Gainesville, FL (US)

(72) Inventors: Chelsea Marie Magin, Denver, CO (US); Shravanthi T. Reddy, Goleta, CA (US); Anthony B. Brennan, Gainesville, FL (US); Rhea Marie May, Morrison, OH (US); Ethan Eugene Mann, Aurora, CO (US); Michael Ryan Mettetal, Denver, CO (US)

(73) Assignees: UNIVERSITY OF FLORIDA RESEARCH FOUNDATION, INC., Gainesville, FL (US); SHARKLET TECHNOLOGIES, INC., Aurora, CO (US)

( * ) Notice: Subject to any disclaimer, the term of this patent is extended or adjusted under 35 U.S.C. 154(b) by 484 days.

(21) Appl. No.: 15/502,359

(22) PCT Filed: Aug. 7, 2015

(86) PCT No.: PCT/US2015/044238
§ 371 (c)(1),
(2) Date: Feb. 7, 2017

(87) PCT Pub. No.: WO2016/022933
PCT Pub. Date: Feb. 11, 2016

(65) Prior Publication Data
US 2017/0216543 A1     Aug. 3, 2017

Related U.S. Application Data

(60) Provisional application No. 62/034,401, filed on Aug. 7, 2014.

(51) Int. Cl.
*A61M 16/04* (2006.01)
*A61F 2/00* (2006.01)
(Continued)

(52) U.S. Cl.
CPC .......... *A61M 16/04* (2013.01); *A61F 2/0077* (2013.01); *A61F 2/1601* (2015.04); *A61M 25/00* (2013.01);
(Continued)

(58) Field of Classification Search
CPC ........ A61F 2/0077; A61F 2/16; A61F 2/1601; A61F 2002/009; A61F 2250/0026;
(Continued)

(56) References Cited

U.S. PATENT DOCUMENTS

| 5,282,851 A | 2/1994 | Jacob-Labarre |
| 5,405,385 A | 4/1995 | Heimke et al. |

(Continued)

FOREIGN PATENT DOCUMENTS

| CN | 2573986 Y | 9/2003 |
| CN | 202459710 U | 10/2012 |

(Continued)

OTHER PUBLICATIONS

International Search Report and Written Opinion for Application No. PCT/US2015/044238 dated Nov. 11, 2015.
(Continued)

*Primary Examiner* — Nilay J Shah
(74) *Attorney, Agent, or Firm* — Cantor Colburn LLP

(57) ABSTRACT

An article includes a path that extends across at least a portion of a surface of the article, the path being defined by at least one channel that traverses at least a portion of the surface or a first plurality of spaced features disposed on or in at least a portion of the surface. The first plurality of spaced features are arranged in a plurality of groupings. The
(Continued)

groupings of features comprise repeat units, where the spaced features within a grouping are spaced apart at an average distance of about 1 nanometer to about 500 micrometers to define a path that traverses the plurality of spaced features.

13 Claims, 31 Drawing Sheets

(51) Int. Cl.
  *A61F 2/16* (2006.01)
  *A61M 25/00* (2006.01)
  *F16L 9/12* (2006.01)
  *F28F 1/00* (2006.01)

(52) U.S. Cl.
  CPC .................................. *F16L 9/12* (2013.01); *F28F 1/00* (2013.01); *A61F 2002/009* (2013.01); *A61F 2250/0026* (2013.01); *A61F 2250/0051* (2013.01); *A61F 2250/0056* (2013.01); *A61F 2250/0068* (2013.01)

(58) Field of Classification Search
  CPC .... A61F 2250/0051; A61F 2002/0086; A61M 25/00; F28F 1/00; B08B 17/06; B08B 17/065; B81C 1/00023; B81C 1/00031; B81C 1/00047; B81C 1/00055; B81C 1/00063; B81C 1/00071; B81C 1/00087; B81C 1/00103; B81C 1/00111; B81C 1/00119
  See application file for complete search history.

(56) References Cited

U.S. PATENT DOCUMENTS

| | | | |
|---|---|---|---|
| 5,833,641 A | 11/1998 | Curtis et al. | |
| 6,399,368 B1 | 6/2002 | Ward | |
| 6,399,693 B1 | 6/2002 | Brennan et al. | |
| 6,667,368 B1 | 12/2003 | Brennan et al. | |
| 7,169,853 B2 | 1/2007 | Brennan et al. | |
| 10,368,978 B2 | 8/2019 | Hyun | |
| 2001/0034552 A1 | 10/2001 | Young et al. | |
| 2002/0183844 A1 | 12/2002 | Fishman et al. | |
| 2004/0086674 A1* | 5/2004 | Holman | A61M 25/0014 428/36.9 |
| 2005/0119758 A1 | 6/2005 | Alexander et al. | |
| 2007/0017633 A1* | 1/2007 | Tonkovich | B01J 19/0093 156/300 |
| 2007/0280994 A1 | 12/2007 | Cunanan | |
| 2008/0077238 A1 | 3/2008 | Deacan et al. | |
| 2010/0033818 A1 | 2/2010 | Petcavich et al. | |
| 2010/0119755 A1 | 5/2010 | Chung et al. | |
| 2010/0226943 A1* | 9/2010 | Brennan | A61L 2/02 424/400 |
| 2011/0098808 A1 | 4/2011 | Kobayashi et al. | |
| 2011/0098811 A1 | 4/2011 | Hong et al. | |
| 2012/0232649 A1 | 9/2012 | Cuevas | |
| 2012/0319325 A1 | 12/2012 | Chung et al. | |
| 2013/0268071 A1 | 10/2013 | Vilupuru et al. | |
| 2013/0304205 A1 | 11/2013 | Cuevas | |
| 2014/0135916 A1 | 5/2014 | Clauson et al. | |
| 2016/0123846 A1 | 5/2016 | Magin et al. | |
| 2017/0152338 A1 | 6/2017 | Brennan et al. | |
| 2018/0078423 A1 | 3/2018 | Magin et al. | |
| 2018/0171157 A1 | 6/2018 | Magin et al. | |
| 2018/0214600 A1 | 8/2018 | Magin et al. | |
| 2019/0161627 A1 | 5/2019 | Brennan et al. | |
| 2019/0202109 A1 | 7/2019 | Stoneberg et al. | |
| 2019/0224903 A1 | 7/2019 | Thielman et al. | |

FOREIGN PATENT DOCUMENTS

| | | |
|---|---|---|
| CN | 202459720 U | 10/2012 |
| EP | 0732090 A1 | 9/1996 |
| EP | 2 305 178 A1 | 4/2011 |
| EP | 2 706 952 A2 | 3/2014 |
| EP | 2 778 753 A2 | 9/2014 |
| WO | WO 93/09732 A1 | 5/1993 |
| WO | 2008036674 A1 | 3/2008 |
| WO | WO 2012/154862 A2 | 11/2012 |
| WO | 2019060555 A2 | 3/2019 |

OTHER PUBLICATIONS

Reddy, S.T. et al., *Micropatterned Surfaces for Reducing the Risk Catheter-Associated Urinary Tract Infection: An In Vitro Study on the Effect of Sharklet Micropatterned Surfaces to Inhibit Bacterial Colonization and Migration of Uropathogenic Escherichia coli*, Journal of Endourology, vol. 25, No. 9 (Sep. 2011) pp. 1547-1552.
Reddy, S. et al., *Micro-Patterned Surfaces for Reducing Bacterial Migration Associated With Catheter-Associated Urinary Tract Infection*, American Journal of Infection Control; 39(5); (Jun. 2011), E37-38.
Graham et al.; "Nano and Microscale Topographies for the Prevention of Bacterial Surface Fouling"; Coatings; 4; 2014, pp. 37-59.
Extended European Search Report for Application No. EP 15829185.6 dated May 7, 2018, 11 pages.
U.S. Appl. No. 16/346,957, filed May 2, 2019.
U.S. Appl. No. 16/356,332, filed Mar. 18, 2019.

* cited by examiner

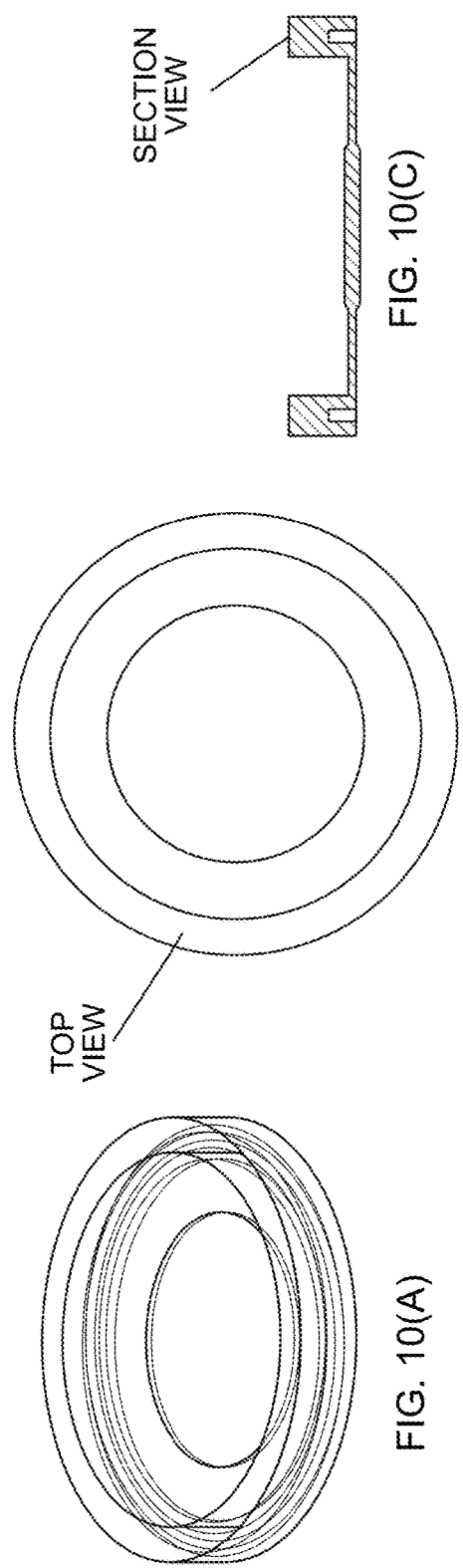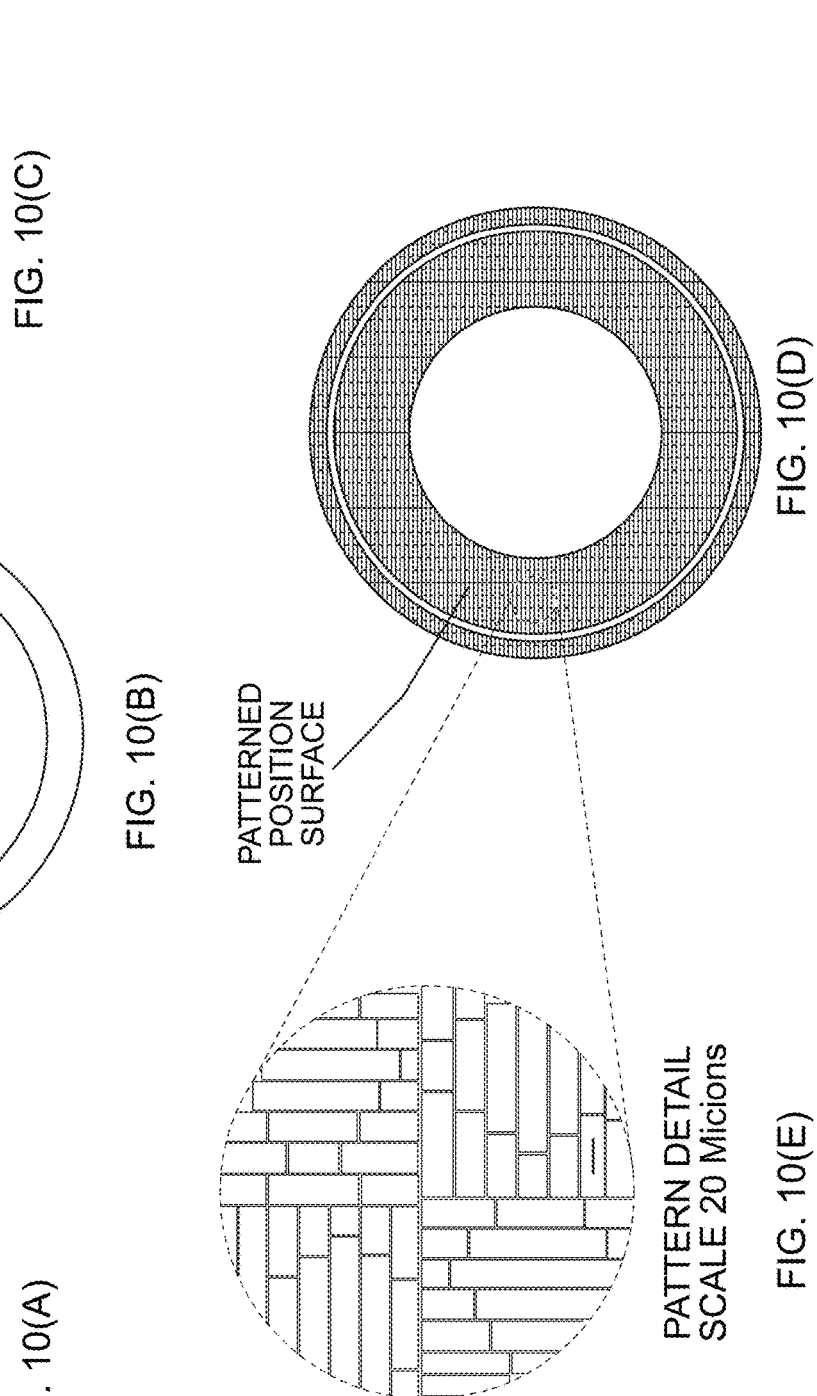

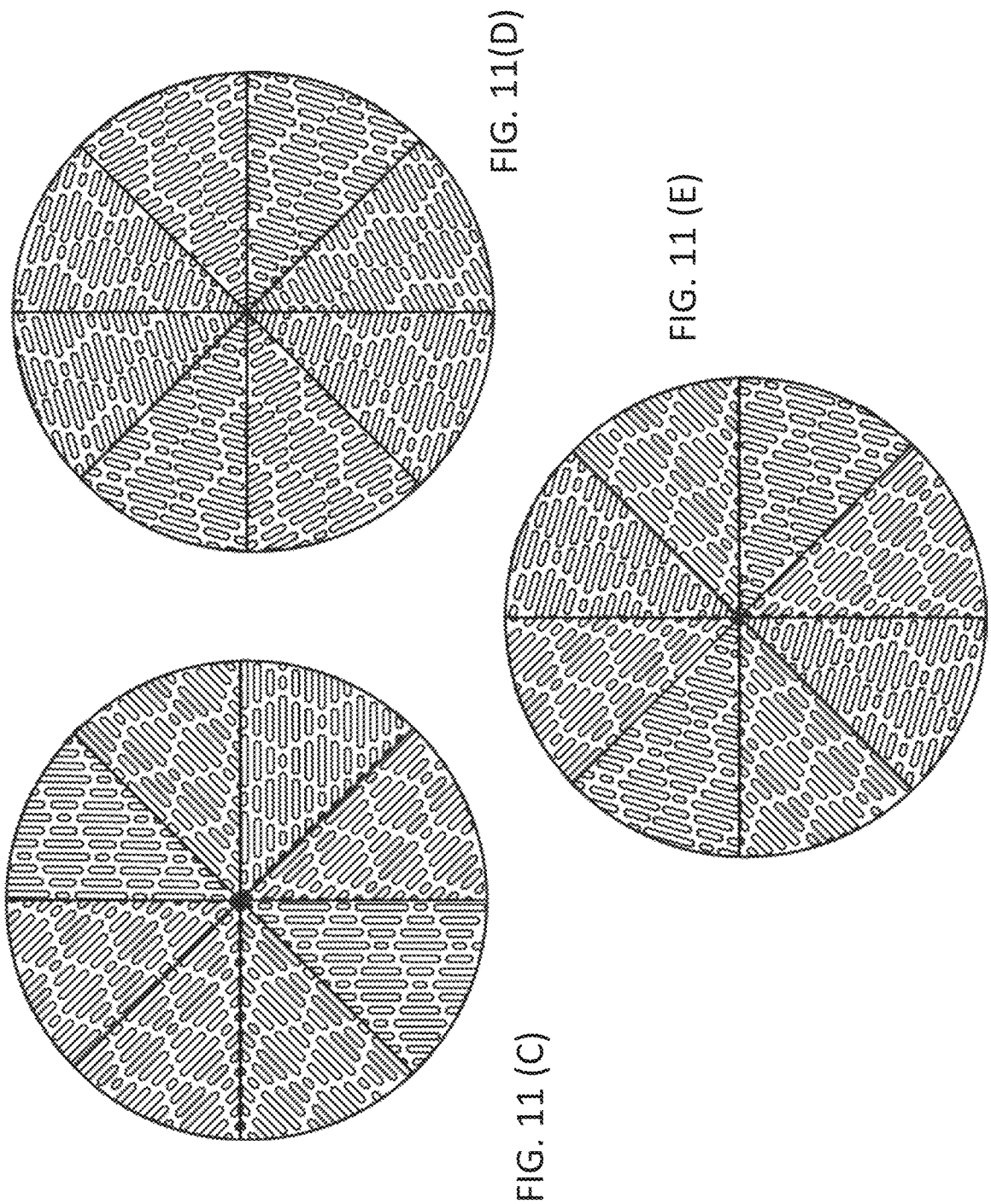

Radial Sharklet Pattern

Radial Sharklet Pattern

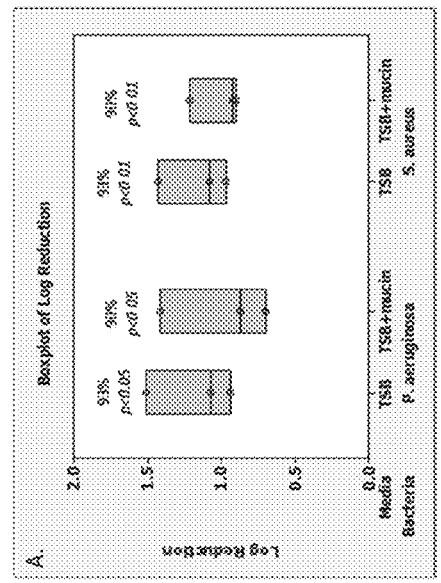
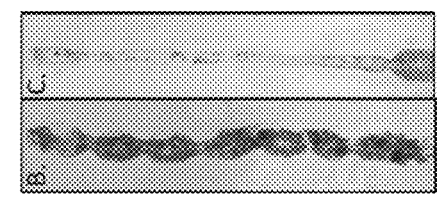
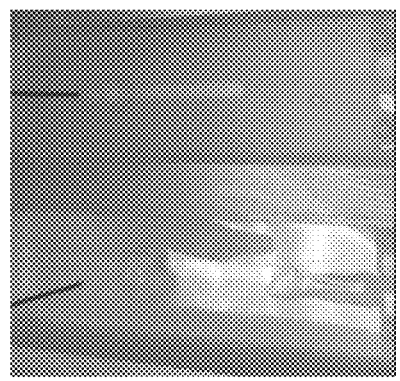
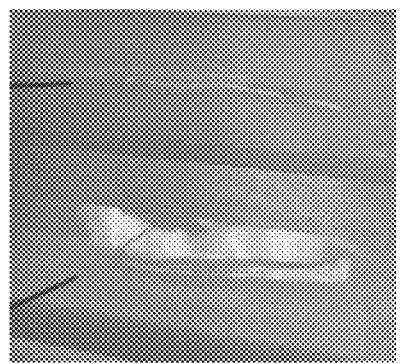
FIG. 19(A)  FIG. 19(B)  FIG. 19(C)  FIG. 19(D)  FIG. 19(E)

PATTERNS FOR FLOW CONTROL AND BIOADHESION CONTROL

CROSS REFERENCE TO RELATED APPLICATIONS

This application is a National Stage application of PCT/US2015/044238, filed Aug. 7, 2015, which claims the benefit of U.S. Provisional Application No. 62/034,401, filed Aug. 7, 2014, both of which are incorporated by reference in their entirety herein.

BACKGROUND

This disclosure relates to patterns for flow control, bioadhesion control, air control and migration control.

Fluids often travel across surfaces that are used to contain them. Surfaces can be planar (i.e., flat) or non-planar (i.e., curved). Examples of flat surfaces are aquariums, dishes used for preparing foods, flat devices used in medical examination, knives used to make incisions during surgery, microfluidic devices, and the like. Devices having curved surfaces are also used in environments where fluids are present. For example, cylindrical curved surfaces (e.g., conduits) are used to transport fluids. Curved surfaces are used to affect attachment of one component to another (e.g., ball and socket, contact lenses on an eyeball, intraocular lenses in the eye, and the like), and fluids are desirable in such regions to effect lubrication.

Fluids that are transported or that travel across these surfaces can be pure fluids (without particles or suspended matter), but often such fluids contain suspended matter in the form of particles and cells. It is often desirable to control the flow of the fluid, the flow of the suspended particles, or both the flow of the fluid and the flow of the suspended particles.

Surfaces that contact fluids also undergo fouling due to the deposition or adhesion of particulate matter (e.g., fillers, proteins and cells) on the surface. It is therefore desirable to design surfaces that can be used to effect control of bioadhesion and to control fluid flow.

Surfaces may undergo fouling due to cell migration whether propelled by flagella or cilia or driven by cytoplasmic displacement or extension of membrane blebs or by alteration of cytoskeletal structures and adhesions, as in the movement of fibroblasts and epithelial cells with translocation occurring as individual cells or in groups, including chains of cells and sheet-like layers.

SUMMARY

Disclosed herein is an article comprising a path that extends across at least a portion of a surface of the article, the path being defined by at least one channel that traverses at least a portion of the surface of the article or a first plurality of spaced features disposed on or in at least a portion of the surface of the article; the spaced features arranged in a plurality of groupings; the groupings of features comprising repeat units; the spaced features within a grouping being spaced apart at an average distance of about 1 nanometer to about 500 micrometers to define a path that traverses the plurality of spaced features; each feature having a surface that is substantially parallel to a surface on a neighboring feature; each feature being separated from its neighboring feature; the groupings of features being arranged with respect to one another so as to define a tortuous pathway.

The article may be a wound dressing, a catheter, an endotracheal tube, or a prosthetic that can be included within the body of a living being.

Disclosed herein too is a tubular article comprising an outer surface; an inner surface; the inner surface comprising a path that extends across at least a portion of the inner surface, the path being defined by at least one channel that traverses at least a portion of the inner surface or a first plurality of spaced features disposed on or in at least a portion of the inner surface; the spaced features arranged in a plurality of groupings; the groupings of features comprising repeat units; the spaced features within a grouping being spaced apart at an average distance of about 1 nanometer to about 500 micrometers to define a path that traverses the plurality of spaced features; the groupings of features being arranged with respect to one another so as to define a tortuous pathway; where the spaced features are effectively arranged to permit the flow of a fluid from one end of the tubular article to another without any spreading across the inner circumference of the tube.

BRIEF DESCRIPTION OF THE FIGURES

FIG. 10(A) depicts a side perspective view of the intraocular lens;

FIG. 10(B) shows a top view of the intraocular lens;

FIG. 10(C) shows a cross-section view of the intraocular lens;

FIG. 10(D) shows a patterned surface on the posterior of the intraocular lens;

FIG. 10(E) shows an inset of the patterned surface in detail;

FIG. 19(A) shows the log reductions of both *Pseudomonas aeruginosa* bifA and *Staphylococcus aureus* on -3 SK-NT2×2.

FIG. 19(B) shows the *Pseudomonas aeruginosa* bifA biofilm reduction on smooth thermoplastic polyurethane (TPU);

FIG. 19(C) shows the *Pseudomonas aeruginosa* bifA biofilm reduction on micropatterned thermoplastic polyurethane (TPU);

FIG. 19(D) shows the controlled and narrowed nature of growth media flow down a micro-patterned surface;

FIG. 19(E) shows the controlled and narrowed nature of growth media flow down a smooth surface;

DETAILED DESCRIPTION

Disclosed herein are devices that contain textured surfaces that can be used to control the flow of fluids, the adhesion of particles and the migration of particles across surfaces of an article or device. The surfaces can be flat or curved and can be internal and/or external surfaces of the device. Fluid, adhesion and migration control can be achieved by orienting the texture at different angles to the direction of fluid flow depending upon the application. The textured surfaces can have continuous paths or alternatively have discontinuous patterns disposed thereon. In an embodiment, the textured surface can have both continuous paths as well as discontinuous patterns disposed thereon.

Fluid flow as defined herein involves both the flow of the fluid and/or of the flow of matter suspended in the fluid. The texturing will henceforth be described in terms of a pattern. The basic unit of the texture is the pattern.

Figure 1:
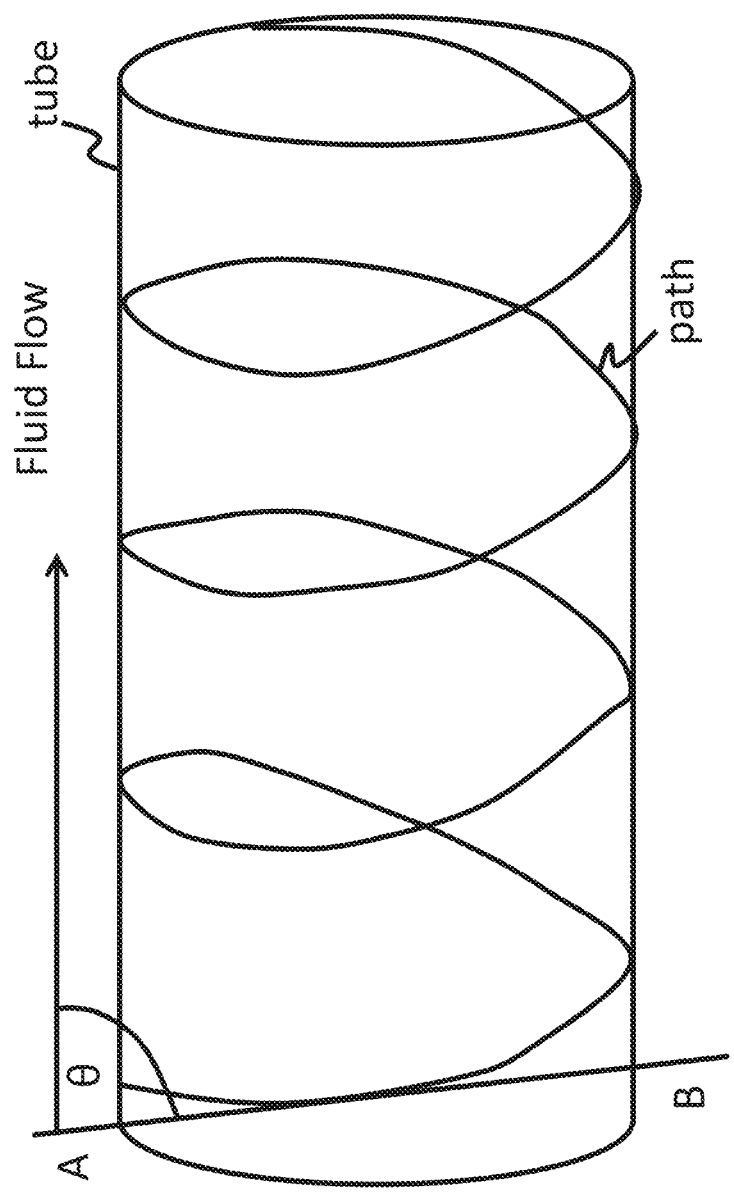
FIG. 1 depicts a cross-section of an embodiment of the defined path that is at least one channel that traverses the at least a portion of the surface of the article but that extends from one end to an opposing end of the article.

In one embodiment, a pattern comprises a continuous path that extends across a surface of a tubular article for its entire length, the path being defined by at least one continuous channel that traverses at least a portion of the surface of the article for at least more than 50%, preferably at least more than 70% and preferably at least more than 90% of the total length of the article In an embodiment, the continuous path extends across the surface of the tubular article for 100% of the total length of the article. Referring to FIG. 1, in an embodiment, the pattern is a curvilinear channel that extends across at least a portion of the surface of a tubular article such as a catheter or an endotracheal tube. In an embodiment, the article comprises a plurality of continuous paths that are defined by a plurality of continuous channels that traverse at least a portion of the tubular surface of the article for at least more than 50%, preferably at least more than 70% and preferably at least more than 90% of the total length of the article of the total length of the article. In an embodiment, the plurality of continuous paths comprise a plurality of continuous channels extend across the surface of the tubular article for 100% of the total length of the article. In an embodiment, the entire tubular surface of the article has disposed on it a plurality of continuous paths that comprise a plurality of continuous channels and that extend for 100% of the total length of the article.

The continuous path is defined by a continuous channel that preferably extends from one end to an opposing surface of the tubular surface. A continuous channel is a trench bounded by walls where a fluid once introduced into the channel cannot escape except over the walls or at the open ends. The continuous path may be oriented such that the channel is oriented to be substantially parallel to the direction of fluid flow or substantially perpendicular to the direction of fluid flow. The continuous path comprising the continuous channel may be disposed on the outside of the tube, the inside of the tube, or on both the inside and the outside of the tube. While the aforementioned embodiments are directed to tubes, conduits have cross-sectional geometries other than a circular geometry may considered. For example, the cross-sectional geometry may be elliptical, square, triangular or polygonal.

The FIG. 1 depicts a tube where the path is substantially perpendicular to the direction of flow of the fluid. The angle between the direction of the path (as measured by a tangent AB to the path) and the direction of flow when both are projected onto a common plane varies from 60 to 120 degrees. In an embodiment, when the tube is an urinary catheter, the path (the term path is inclusive of the plurality of paths) is disposed on the outside of the tube and/or on the inside of the tube and is oriented to be substantially perpendicular to the direction of flow, preferably oriented at an angle of 60 to 120 degrees, preferably 70 to 110 degrees, and more preferably 80 to 100 degrees to the direction of flow. In an embodiment, when the tube is an urinary catheter, the path is disposed on the outside of the tube and covers substantially all of the available outer surface of the tube. In another embodiment, when the tube is an urinary catheter, a first path disposed on the outside of the tube may be inclined at 60 to 120 degrees to the direction of fluid flow (where the fluid flow occurs inside the tube), while a second path disposed on the inside of the tube may be inclined at an angle of −45 to +45 degrees, preferably −35 to +35 degrees, preferably −25 to +25 degrees and more preferably −15 to +15 degrees to the direction of flow to the direction of fluid flow on the inside of the tube. In yet another embodiment, when the tube is an urinary catheter, a first path disposed on the outside of the tube may be inclined at 60 to 120 degrees to the direction of fluid flow (where the fluid flow occurs inside the tube), while the inside of the tube may have a smooth surface without any paths disposed thereon.

Figure 2:
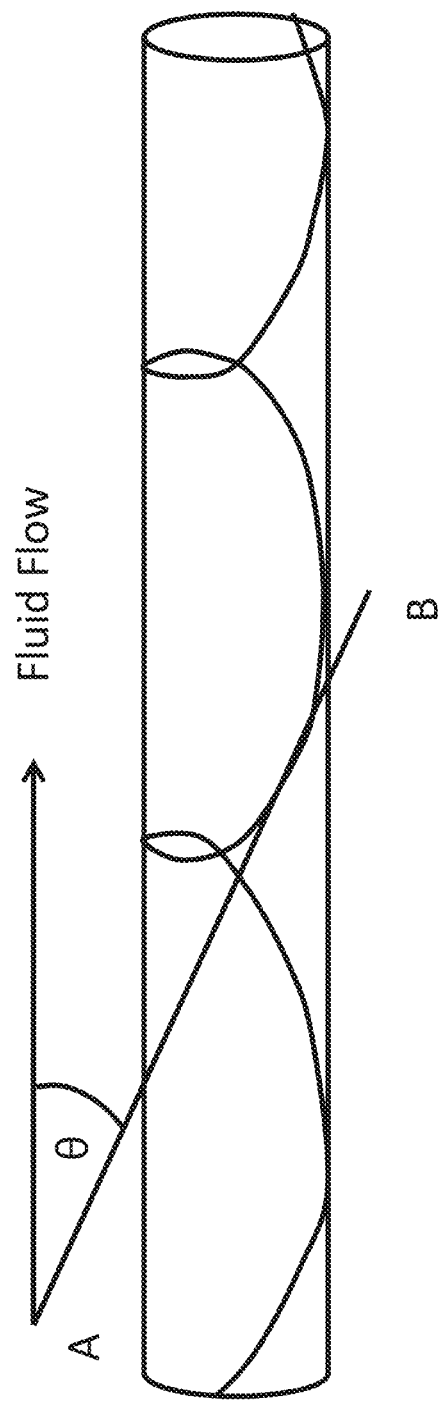
FIG. 2 depicts a cross-section of another embodiment of the defined path that is at least one channel that traverses the at least a portion of the surface of the article but that extends from one end to an opposing end of the article.

The FIG. 2 depicts a tube where the path is substantially parallel to the direction of flow of the fluid. The angle between the direction of the path (as measured by a tangent AB to the path) and the direction of flow when both are projected onto a common plane varies from −45 degrees to +45 degrees. In an embodiment, when the tube is an endotracheal tube, the path (the term path is inclusive of the plurality of paths) is disposed on the outside of the tube and/or on the inside of the tube and is oriented to be substantially parallel to the direction of flow, preferably oriented at an angle of −45 to +45 degrees, preferably −35 to +35 degrees, preferably −25 to +25 degrees and more preferably −15 to +15 degrees to the direction of flow. In an embodiment, when the tube is an endotracheal tube, the path is disposed on the inside of the tube and covers substantially all of the available outer surface of the tube. The continuous paths of the FIGS. 1 and 2 may be linear or curvilinear. In an embodiment, the continuous path is curvilinear and is preferably helical.

Disclosed herein too are conduits that comprise patterns disposed on the surfaces. Each pattern comprises a plurality of spaced features (also termed elements) arranged in a manner so as to form a tortuous path between the patterns. In some embodiments, the elements are arranged in such a manner to form a tortuous path between the elements of successive patterns. A plurality of patterns is called a grouping. The pattern is repeated over numerous times to form the texture on the surface. In other words, the groupings form a texture on the surface. In one embodiment, in order to control flow, the texture is applied in the form of grids where each grid contains a pattern that is inclined at different angles in different grids. An exemplary embodiment of one of the patterns is shown in the FIG. 3(A). In the FIG. 3(A), there are 4 grids numbered 1 through 4 and it may be seen that patterns in adjacent grids are inclined with respect to each other. Each pattern has an axis (denoted by the lines A-A' and the lines B-B' respectively). With regard to the patterns shown in the FIG. 3(A), the axes A-A' and B-B' respectively are lines that pass through the geometric center of the repeat pattern. The geometric center is the center of mass of the pattern (i.e., the elements of the pattern without the substrate).

Figure 3A:
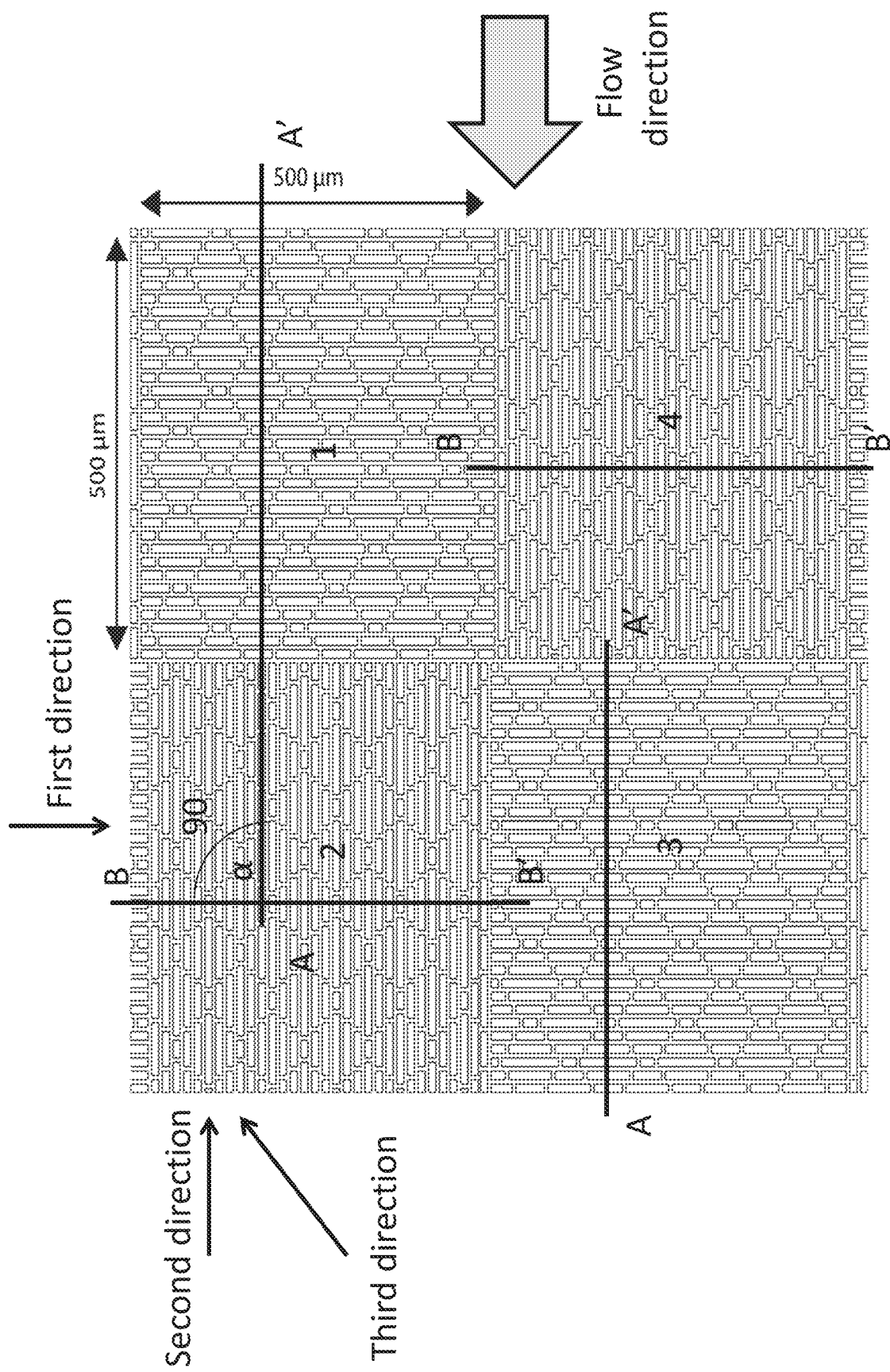
FIG. 3(A) depicts 4 grids numbered 1 through 4 where the patterns in adjacent grids are inclined with respect to each other.

From the FIG. 3(A), it may be seen that the axes A-A' and B-B' are inclined to each other at an angle α of approximately 90 degrees. The angle α may be varied from 5 degrees to 175 degrees, preferably 20 to 150 degrees and more preferably 70 to 120 degrees.

By rotating the patterns in one grid relative to the pattern orientation in a neighboring grid with respect to each other, the resistance to flow in one grid can be varied with respect to that of the neighboring grid.

The pattern in each of the grids comprises a plurality of spaced features where the patterns arranged in a plurality of groupings and where the groupings of patterns are arranged with respect to one another so as to define a tortuous pathway over a portion of the texture when viewed in a first direction. When viewed in a second direction (in the same grid) that is perpendicular to the first direction (but in the same plane as the first direction), the groupings of features are arranged to define a linear pathway over a portion of the texture.

As can be seen in the FIG. 3(A), the aspect ratio of the neighboring elements in a given pattern are different from each other in both the first direction and the second direction. It is desirable for each grid to have at least some elements where the aspect ratio is greater than 1, preferably greater than 2, preferably greater than 3, preferably greater than 4, preferably greater than 5, and more preferably greater than 10. In each pattern, there are at least two elements that are different from one another, preferably at least three elements that are different from each other and more preferably at least four elements that are different from each other.

Figure 3B:
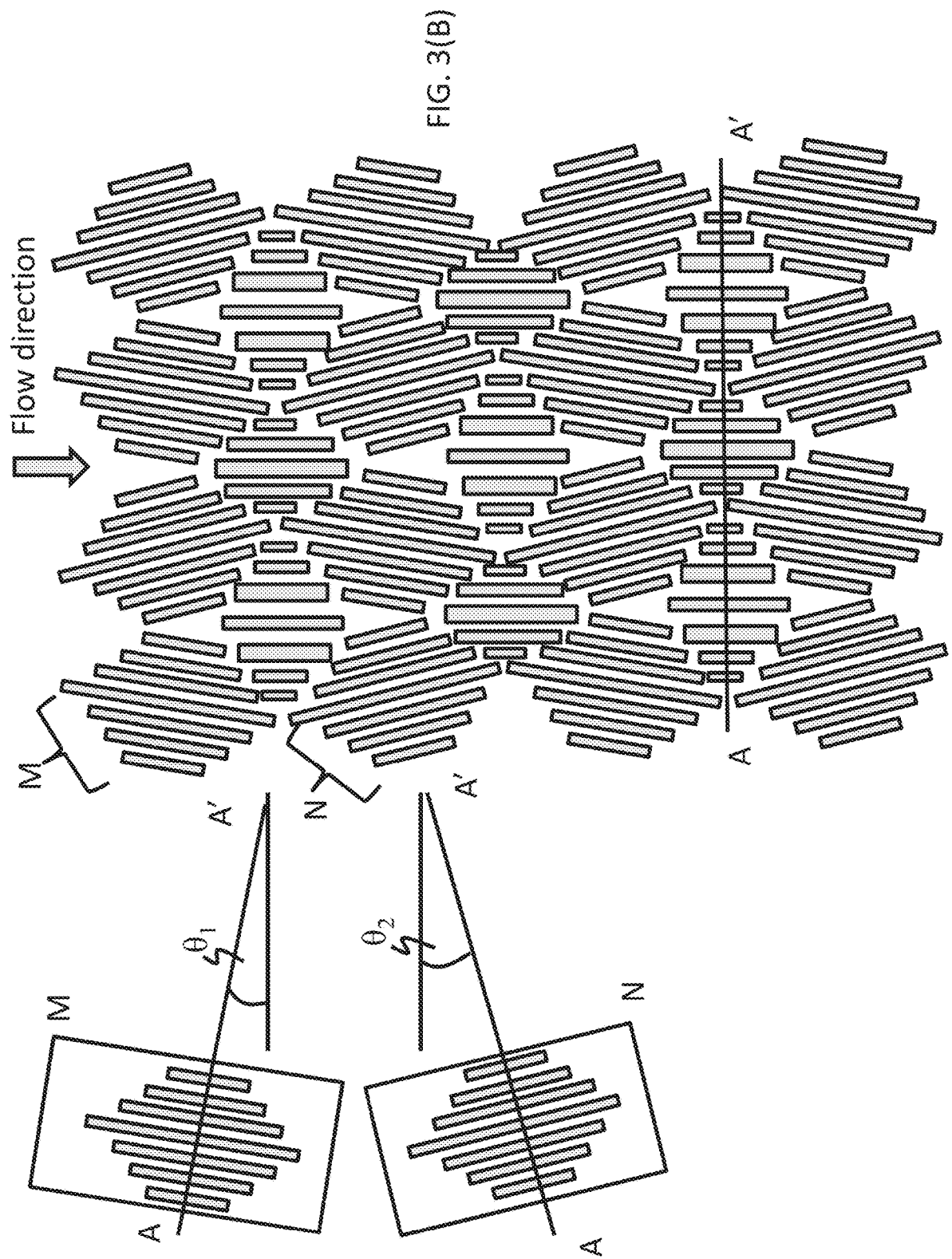
FIG. 3(B) shows at least two sets of patterns whose elements are different from each other and where the patterns are arranged in a manner effective to produce tortuous paths between the elements as well as between the patterns.

FIG. 3(B) shows another pattern where the plurality of spaced features are oriented in different directions with respect to the direction of fluid flow. FIG. 3(B) shows at least two sets of patterns whose elements are different from each other and where the patterns are arranged in a manner effective to produce tortuous paths between the elements as well as between the patterns. From the patterns M and N of the FIG. 3(B), it can be seen that some elements of successive patterns M and N are arranged in the form of a sinusoidal curve and that similar patterns of the texture have a periodicity to them in mutually perpendicular directions. By varying angles $\theta_1$ and $\theta_2$ with respect to the direction of flow, fluids that contact the surface can be made to flow at different velocities. The patterns can also be used to control the flow of particulate matter (such as cells, bacteria, fillers, and the like) contained in a fluid especially when the texture is disposed on an inner curved surface of articles such as conduits. Centrifugal forces in the fluid can cause particulate matter to be propelled towards the textured walls of the conduit where the texturing acts to control particle velocity. Pattern sizes and element sizes can be varied to control particulate flow (both velocity and direction).

In one embodiment, the presence of the texture alters contact angles of a fluid on the substrate and this can be used to promote unidirectional flow or can be used to cause the flow to diverge in different directions.

In the FIG. 3(B), $\theta_1$ and $\theta_2$ can vary from 5 degrees to 50 degrees to a line (an axis AA') that is drawn perpendicular to the direction of flow. In short, the axis A-A' of a pattern which is perpendicular to at least one of the elements of the pattern and passes through a center of mass of the pattern varies from 5 degrees to 50 degrees to a line that is drawn perpendicular to the direction of flow. In one embodiment, the axis of a pattern is perpendicular to at least two of the elements of the pattern and passes through the center of mass of the pattern. In another embodiment, the axis of a pattern is perpendicular to at least three of the elements of the pattern and passes through the center of mass of the pattern. In yet another embodiment, the axis of a pattern is perpendicular to at least four of the elements of the pattern and passes through the center of mass of the pattern. In yet another embodiment, the axis of a pattern is perpendicular to all elements of the pattern and passes through the center of mass of the pattern. In one embodiment, in the FIG. 3(B), it may be seen that some of the patterns are arranged such that their axes are perpendicular to the direction of flow. The FIG. 3(B) thus encompasses at least two sets of different patterns (one with its axis perpendicular to the direction of flow and another with axes that are inclined to the direction of flow) that are combined together to produce the texture. The pattern of the FIG. 3(B) may be rotated with respect to the direction of flow such that axes that are perpendicular to the direction of flow can be parallel to the direction of flow or can be inclined to the direction of flow.

Figure 4A:
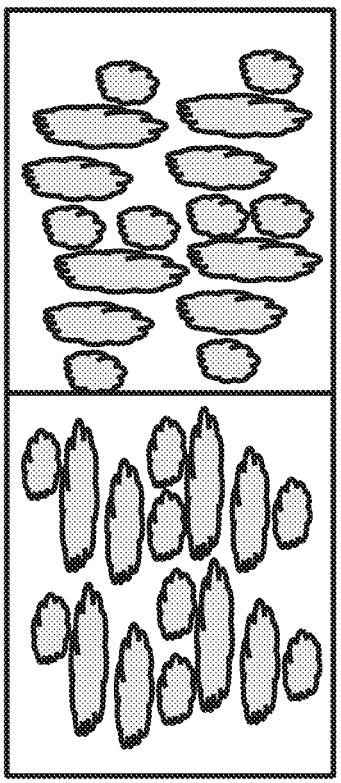
FIG. 4(A) shows how elements having regular geometries can be used to control flow by having grids adjacent to each other contain differently oriented elements.
Figure 4B:
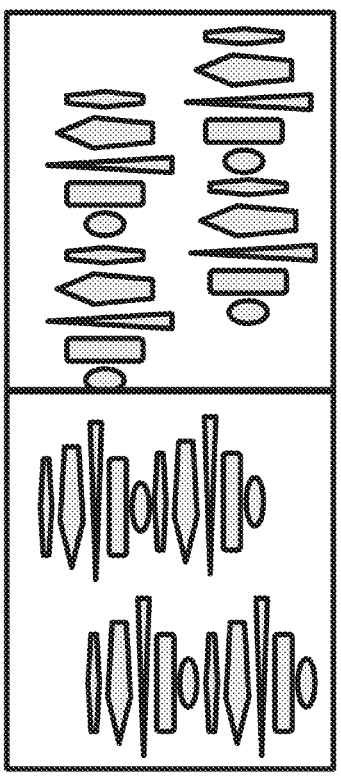
FIG. 4(B) shows how elements having irregular geometries can be used to control flow by having grids adjacent to each other contain differently oriented elements.
Figure 4C:
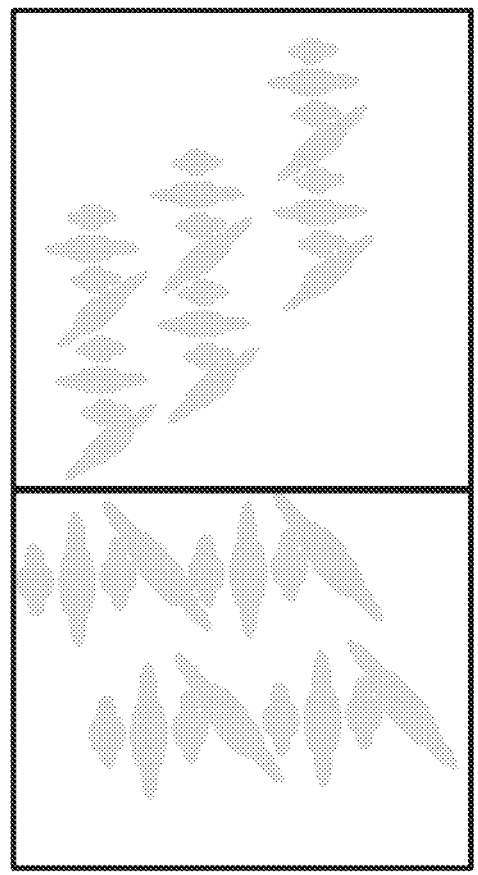
FIG. 4(C) shows how elements having combinations of regular and irregular geometries can be used to control flow by having grids adjacent to each other contain differently oriented elements.

FIG. 4 shows other patterns that comply with the aforementioned definition of the patterns. FIG. 4(A) shows how elements having regular geometries can be used to control flow by having grids adjacent to each other contain differently oriented elements. FIG. 4(B) shows how elements having irregular geometries can be used to control flow by having grids adjacent to each other contain differently oriented elements. FIG. 4(C) shows how elements having combinations of regular and irregular geometries can be used to control flow by having grids adjacent to each other contain differently oriented elements. In all of the FIGS. 4(A) through 4(C), at least some of the elements of the pattern have aspect ratios greater than 1.

In one embodiment (once again with respect to the FIGS. 3(A) and 3(B)), when viewed in a third direction that is inclined at 45 degrees to the second direction, the pathway between the features may be non-linear and non-sinusoidal. In other words, the pathway can be non-linear and aperiodic. In another embodiment, the pathway between the features may be linear but of a varying thickness. The plurality of spaced features may be projected outwards from a surface or projected into the surface. In one embodiment, the plurality of spaced features may have the same chemical composition as the surface. In another embodiment, the plurality of spaced features may have a chemical composition different from the surface.

As to particular embodiments, an article having a surface topography for resisting bioadhesion of organisms, comprises a base article having a surface. The composition of the surface and/or the base article comprises a polymer, a metal or an alloy, a ceramic and/or a glass. Combinations of polymers, metals and ceramics may also be used in the surface or the base article. The surface having a topography comprising a plurality of patterns; each pattern being defined by a plurality of spaced apart features attached to or projected into the base article. The plurality of features each have at least one micrometer or nanometer sized dimension and has at least one neighboring feature having a substantially different geometry (i.e., it is different in either shape or size).

The average first feature spacing between the adjacent features is between 5 nanometers and 100 μm in at least a portion of the surface, wherein said plurality of spaced apart features are represented by a periodic function. In one embodiment, each of the features of the plurality of features are separated from each other and do not contact one another. In another embodiment, some of the plurality of features may contact each other.

In another embodiment, the average periodicity between the spaced features can be about 1 nanometer to about 500 micrometers. In one embodiment, the periodicity between the spaced features can be about 2, 5, 10, 20, 50, 100 or 200 nanometers. In another embodiment, the average periodicity between the spaced features can be about 2, 5, 10, 20, 50, 100 or 200 nanometers. In another embodiment, the periodicity can be about 0.1, 0.2, 0.5, 1, 5, 10, 20, 50, 100, 200, 300, 400 or 450 micrometers. In yet another embodiment, the average periodicity can be about 0.1, 0.2, 0.5, 1, 5, 10, 20, 50, 100, 200, 300, 400 or 450 micrometers.

In one embodiment, the spaced features can have dimensions of 1 nanometer to 500 micrometers, specifically about 10 nanometers to about 200 micrometers, and more specifically about 50 nanometers to about 100 micrometers.

In another embodiment, the periodicity between the spaced features can be about 1 nanometer to about 500 micrometers. In one embodiment, the periodicity between the spaced features can be up to about 2, 5, 10, 20, 50, 100 or 200 nanometers. In another embodiment, the periodicity between the spaced features can be about 2, 5, 10, 20, 50, 100 or 200 nanometers. In another embodiment, the periodicity can be up to about 0.1, 0.2, 0.5, 1, 5, 10, 20, 50, 100, 200, 300, 400 or 450 micrometers. In yet another embodiment, the periodicity can be up to about 0.1, 0.2, 0.5, 1, 5, 10, 20, 50, 100, 200, 300, 400 or 450 micrometers.

In one embodiment, each feature of a pattern has at least one neighboring feature that has a different geometry (e.g., size or shape). A feature of a pattern is a single element. Each feature of a pattern has at least 2, 3, 4, 5, or 6 neighboring features that have a different geometry from the feature. In one embodiment, there are at least 2 or more different features that form the pattern. In another embodiment, there are at least 3 or more different features that form the pattern.

In yet another embodiment, there are at least 4 or more different features that form the pattern. In yet another embodiment, there are at least 5 or more different features that form the pattern.

In another embodiment, at least two identical features of the pattern have at least one neighboring feature that has a different geometry (e.g., size or shape). A feature of a pattern is a single element. In one embodiment, two identical features of the pattern have at least 2, 3, 4, 5, or 6 neighboring features that have a different geometry from the identical features. In another embodiment, three identical features of the pattern have at least 2, 3, 4, 5, or 6 neighboring features that have a different geometry from the identical features.

In another embodiment, each pattern has at least one or more neighboring patterns that have a different size or shape. In other words, a first pattern can have a second neighboring pattern that while comprising the same features as the first pattern can have a different shape from the first pattern. In yet another embodiment, each pattern has at least two or more neighboring patterns that have a different size or shape. In yet another embodiment, each pattern has at least three or more neighboring patterns that have a different size or shape. In yet another embodiment, each pattern has at least four or more neighboring patterns that have a different size or shape.

As noted above the chemical composition of the spaced features can be different from the surface. The spaced features and the surfaces from which these features are projected or projected into can also comprise organic polymers or inorganic materials. Composites can also be used.

Organic polymers used in the spaced features and/or the surface may be selected from a wide variety of thermoplastic polymers, blend of thermoplastic polymers, thermosetting polymers, or blends of thermoplastic polymers with thermosetting polymers. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, a polyelectrolyte (polymers that have some repeat groups that contain electrolytes), a polyampholyte (a polyelectrolyte having both cationic and anionic repeat groups), an ionomer, or the like, or a combination comprising at last one of the foregoing organic polymers.

Examples of the organic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination comprising at least one of the foregoing organic polymers.

Examples of polyelectrolytes are polystyrene sulfonic acid, polyacrylic acid, pectin, carageenan, alginates, carboxymethylcellulose, polyvinylpyrrolidone, or the like, or a combination comprising at least one of the foregoing polyelectrolytes.

Examples of thermosetting polymers suitable for use in the polymeric composition include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleicanhydride/acrylonitrile-butadiene-styrene, polyether etherketone/polyethersulfone, polyether etherketone/polyetherimide polyethylene/nylon, polyethylene/polyacetal, or the like.

Polymers that can be used for the pattern or the substrate include biodegradable materials. Suitable examples of biodegradable polymers are as polylactic-glycolic acid (PLGA), poly-caprolactone (PCL), copolymers of polylactic-glycolic acid and poly-caprolactone (PCL-PLGA copolymer), polyhydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), or the like, or combinations comprising at least one of the foregoing biodegradable polymers. The biodegradable polymers upon undergoing degradation can be consumed by the body without any undesirable side effects.

Metals used in the spaced features and/or the surface may be selected from a wide variety of metal alloys, metal composites or combinations with other materials. Examples of metals are stainless steel, carbon steel, copper, brass, gold, gold alloys, nickel, nickel alloy steels, Co—Cr alloys, platinum, platinum alloys, palladium, palladium alloys, titanium, titanium alloys, aluminum, aluminum alloys, zirconium, zirconium alloys, molybdenum, molybdenum alloys, tantalum, tantalum alloys, tungsten, tungsten alloys, cobalt and cobalt alloys, vanadium and vanadium alloys or the like.

Ceramics used in the spaced features and/or the surfaces may be selected from a wide variety of ceramics, ceramic like and porcelain or glass-like combinations including aluminum oxides, barium oxide, molybdenum oxide, calcium oxide, titanium oxides, zirconium oxides, tantalum oxides, silica oxides, or any alloys in addition those alloys not listed but familiar to those skilled in the art. Other examples include those from inorganic-organic hybrid made by the sol-gel process that may be used in the green state or in the sintered state. These may include xerogel and aerogel compositions.

In one embodiment, the pattern can comprise a polymeric resin that is blended with a biologically active agent to form a drug coating. The biologically active agent is then gradually released from the pattern, which simply acts as a carrier. When the polymeric resin is physically blended (i.e., not covalently bonded) with the biologically active agent, the release of the biologically active agent from the drug coating is diffusion controlled. It is generally desirable for the pattern to comprise an amount of about 5 weight percent (wt %) to about 90 wt % of the biologically active agent based on the total weight of the drug coating. Within this range, it is generally desirable to have the biologically active agent present in an amount of greater than or equal to about 10, preferably greater than or equal to about 20, and more preferably greater than or equal to about 30 wt % based on the total weight of the drug coating. Within this range it is generally desirable to have the biologically active agent present in an amount of less than or equal to about 75, preferably less than or equal to about 70, and more preferably less than or equal to about 65 wt % based on the total weight of the drug coating. The drug coating may be optionally coated with an additional surface coating if desired. When an additional surface coating is used, the release of the biologically active agent is interfacially controlled. The drug coating may be disposed only on the surface of the features or alternatively on the surface of the tortuous pathway.

In another exemplary embodiment, the biologically active agent may be covalently bonded with a biodegradable polymer to form the drug coating. The rate of release is then controlled by the rate of degradation of the biodegradable polymer. Suitable examples of biodegradable polymers are provided above. Within this range, it is generally desirable to have the biologically active agent present in an amount of greater than or equal to about 10, preferably greater than or equal to about 20, and more preferably greater than or equal to about 30 wt % based on the total weight of the drug coating. Within this range, it is also generally desirable to have the biologically active agent present in an amount of less than or equal to about 75, preferably less than or equal to about 70, and more preferably less than or equal to about 65 wt %, based on the total weight of the drug coating.

When the pattern is used in a medical device, the drug coating may be coated onto the medical device in a variety of ways. In one embodiment, the drug coating may be dissolved in a solvent such as water, acetone, alcohols such as ethanol, isopropanol, methanol, toluene, dimethylformamide, dimethylacetamide, hexane, and the like, and coated onto the medical device in the form of the pattern. In another embodiment, a monomer may be covalently bonded with the biologically active agent and then polymerized to form the drug coating, which is then applied onto the medical device in the form of the pattern. In yet another embodiment, the polymeric resin may first be applied as a coating (in the form of the pattern) onto the medical device, following which the coated device is immersed into the biologically active agent, thus permitting diffusion into the coating to form the drug coating.

In one embodiment, a biologically active agent can be added to the pattern. The biologically active agent can be disposed upon the surface of the pattern or can be included in the pattern (e.g., mixed with the material forming the pattern). It may also be desirable to have two or more biologically active agents dispersed in a single drug coating layer. Alternatively, it may be desirable to have two or more layers of the drug coating coated upon the medical device. Various methods of coating may be employed to coat the medical device such as spin coating, electrostatic painting, dip-coating, painting with a brush, and the like, and combinations comprising at least one of the foregoing methods of coating.

Various types of biologically active agents may be used in the drug coating, which is used to coat the medical device. The coatings on the medical device may be used to deliver therapeutic and pharmaceutically biologically active agents including anti-analgesic agents, anti-arrhythmic agents, anti-bacterial agents, anti-cholinergic agents, anti-coagulant agents, anti-convulsant agents, anti-depressant agents, anti-diabetic agents, anti-diuretic agents, anti-fungal agents, anti-hypertensive agents, anti-inflammatory agents, anti-malarial agents, anti-neoplastic agents, anti-nootropic agents, anti-Parkinson agents, anti-retroviral agents, anti-tuberculosis agents, anti-tussive agents, anti-ulcerative agents, anti-viral agents, or the like, or a combination comprising at least one of the foregoing therapeutic and pharmaceutically biologically active agents. Biologically active agents may also be proteins, peptide fragments, growth factors or other cell-signaling molecules.

In one embodiment, the surface is monolithically integrated with the base article, wherein the composition of the base article is the same as the composition of the surface. In another embodiment, the surface comprises a coating layer disposed on the base article. In yet another embodiment, the composition of the coating layer is different from the composition of the base article. In one embodiment, the polymer comprises a non-electrically conducting polymer.

The texture and/or the substrate upon which the texture is disposed may be manufactured from a shape memory alloy or a shape memory polymer and its shape can be changed upon the used of an activating signal such as a thermal signal, an electrical signal or the like.

In another embodiment, the topography provides an average roughness factor (R) of from 4 to 50. The surface may comprise an elastomer that has an elastic modulus of about 10 kPa to about 10 MPa.

As noted above, the pattern is separated from a neighboring pattern by a tortuous pathway. The tortuous pathway may be represented by a periodic function. The periodic functions may be different for each tortuous pathway. In one embodiment, the patterns can be separated from one another by tortuous pathways that can be represented by two or more periodic functions. The periodic functions may comprise a sinusoidal wave. In an exemplary embodiment, the periodic function may comprise two or more sinusoidal waves.

In another embodiment, when a plurality of different tortuous pathways are represented by a plurality of periodic functions respectively, the respective periodic functions may be separated by a fixed phase difference. In yet another embodiment, when a plurality of different tortuous pathways are represented by a plurality of periodic functions respectively, the respective periodic functions may be separated by a variable phase difference.

In one embodiment, the plurality of spaced apart features have a substantially planar top surface. In another embodiment, a multi-element plateau layer can be disposed on a portion of the surface, wherein a spacing distance between elements of said plateau layer provide a second feature spacing; the second feature spacing being substantially different when compared to the first feature spacing.

The grids can have different geometries. For example, the grids can be rectangles, squares, triangles, circles, ellipses, polygons or combinations thereof. The side of a grid may be 20 nanometers to 1,000 micrometers. For circular and elliptical grids, the average radius may vary from 10 nanometers to 500 micrometers. In an exemplary embodiment, the grid comprises squares each having a side of 50 micrometers.

The patterns disclosed above in the FIGS. 1 and 2 can be used on the internal and external surfaces of conduits (e.g., catheters, endotracheal tubes, central venous catheters, urethral tubes, shunts that direct fluids away or towards other organs in the bodies of living beings, or the like).

As to particular embodiments, the pattern can be disposed on the surface of articles or devices to be parallel or perpendicular (or other angulation) to the direction of fluid flow or to be parallel or perpendicular (or other angulation) to the direction of cell migration or have portions disposed in part parallel and in part perpendicular (or other angulation) to the direction of cell migration. Cells that migrate or translocate across surfaces, as above described, whether across biological surfaces of an organism, biological or non-biological surfaces implantable in organisms, or non-biological surfaces that may interact with organisms can for examples include: platelets, white blood cells, tissue cells such as endothelial cells, fibroblasts epithelial cells, human lens epithelial cells, bacteria, or the like.

In one embodiment, the patterns are disposed on these surfaces to be parallel and/or perpendicular to the direction of fluid flow or to be parallel and/or perpendicular to the direction of cell migration. Cell migration can include cells that are desirable (such as platelets, red blood cells, white blood cells, tissue cells such as endothelial cells, epithelial cells, or the like) or undesirable cells (such as bacterial cells).

As stated above, the patterns (in the respective grids) may be disposed such that some of the elements of the pattern may be parallel and/or perpendicular to the flow direction of fluids and/or particulate matter contained in the fluids. As noted above, the pattern is parallel to the flow direction when the axis of the pattern is parallel to the flow direction and it is perpendicular, when the axis is perpendicular to the flow direction. For the pattern shown in the FIG. 1, the patterns in some grids will be parallel to the flow direction while those in other adjacent grids will simultaneously be perpendicular to the flow direction of the fluid.

Figure 5:
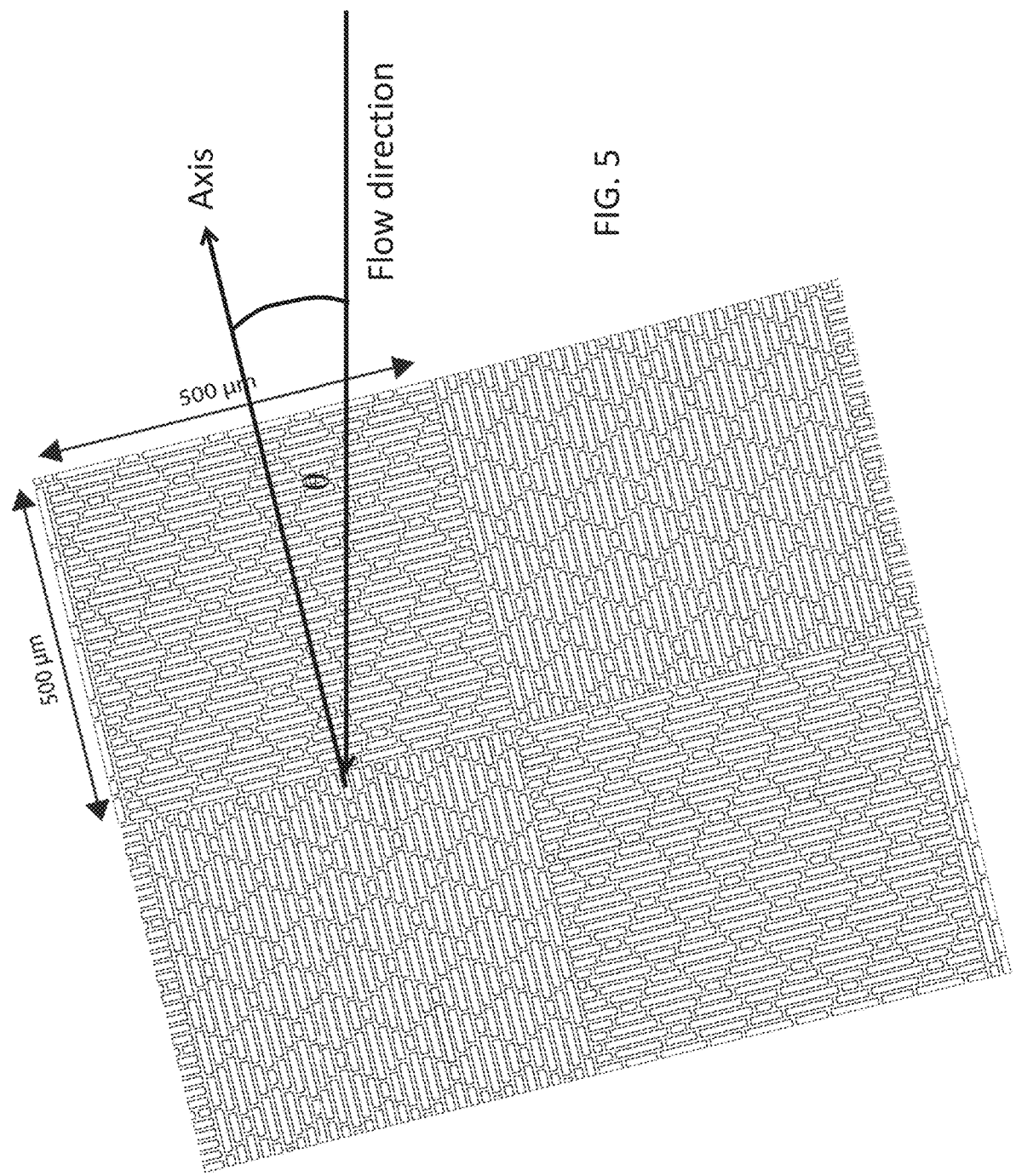
FIG. 5 depicts how the axis of the pattern can be inclined with respect to flow direction.

It is to be noted that the flow direction be at an angle that is neither parallel nor perpendicular to the flow direction, but can be in between. FIG. 5 depicts how the axis of the pattern can be inclined with respect to flow direction. In one embodiment, the axis of the patterns (See FIGS. 3(A) and 3(B) and 5) may be inclined at an angle of 5 to 175 degrees, preferably 15 to 150 degrees, preferably 50 to 135 degrees and more preferably 75 to 125 degrees to the flow direction. In an exemplary embodiment, the patterns in one grid are parallel to the flow direction, while in another grid they are perpendicular to the flow direction.

The patterns may be disposed on the entire surface or only on selected portions of the curved or planar surface. In one embodiment, the patterns may cover 2% or more, preferably 10% or more, preferably 20% or more, preferably 50% or more, and more preferably 75% or more of the surface.

Figure 6:
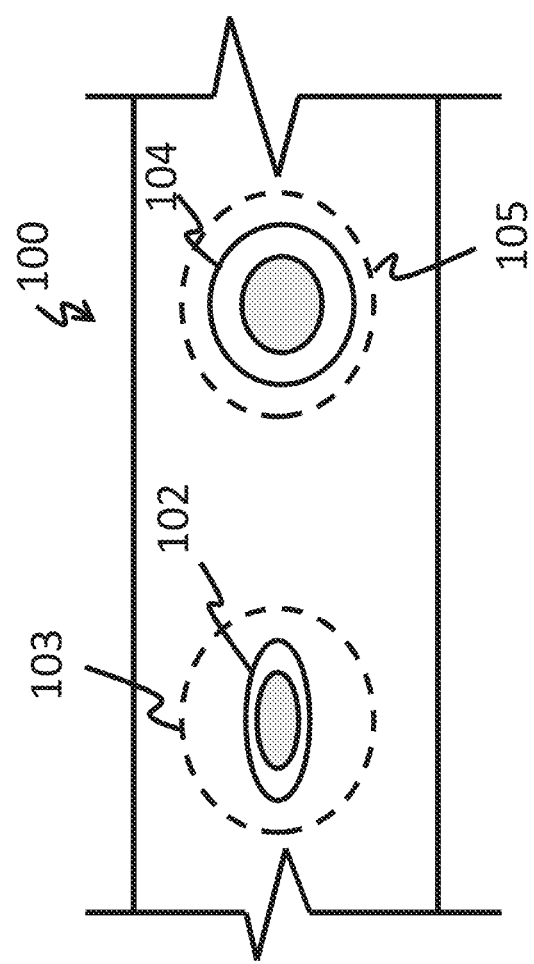
FIG. 6 depicts one example of an application where only a small portion of a conduit surface has the texturing.
Figure 7:
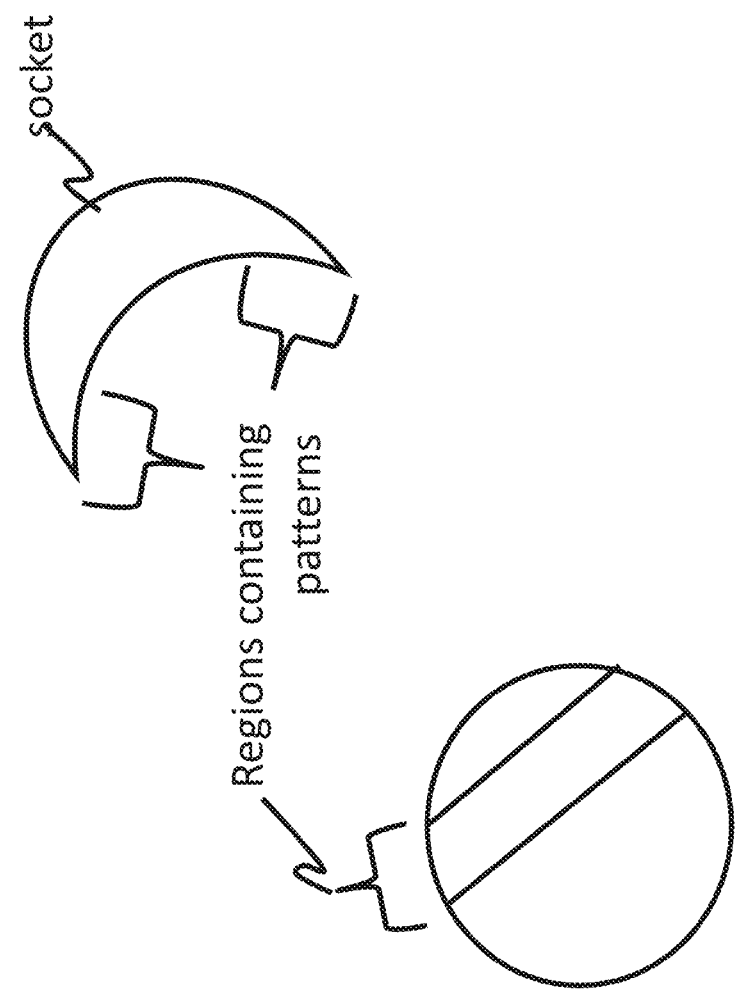
FIG. 7 depicts how the texturing can be disposed on only a portion of a prosthetic such as for example a ball and socket.

The FIG. 6 depicts one example of an application where only a small portion of a conduit surface has the texturing. The conduit 100 has two openings 102 and 104 (also called eyelets) for the feeding or removal of fluids that contact the conduit. The area around each opening 102 and 104 has the pattern of the FIG. 1 disposed in the areas 103 and 105 respectively. The use of the pattern around each opening 102 and 104 prevents the migration of bacteria and extraneous cellular matter into the conduit. An exemplary conduit would be a shunt used for transferring fluids to the body of a living being or removing fluids from the body of the living being. In one embodiment, the pattern can be disposed on spherical or ellipsoidal prosthetic surfaces such as ball and sockets for bone joints. As detailed above, the pattern can be disposed on a portion of the ball and socket so as to prevent migration of cells to the contact point between the ball and socket. Alternatively, the pattern can be disclosed in a manner so as to prevent the flow of cells into the points of contact of the ball and sockets, while permitting other fluids to flow away from the points of contact of the ball and socket. FIG. 7 shows a section of a ball and socket with only a portion of the socket and a portion of the ball having patterns disposed thereon. The orientation of the patterns and the dimensions of the patterns can be adjusted based upon the types of cells that are desired in the contact area.

Figure 8:
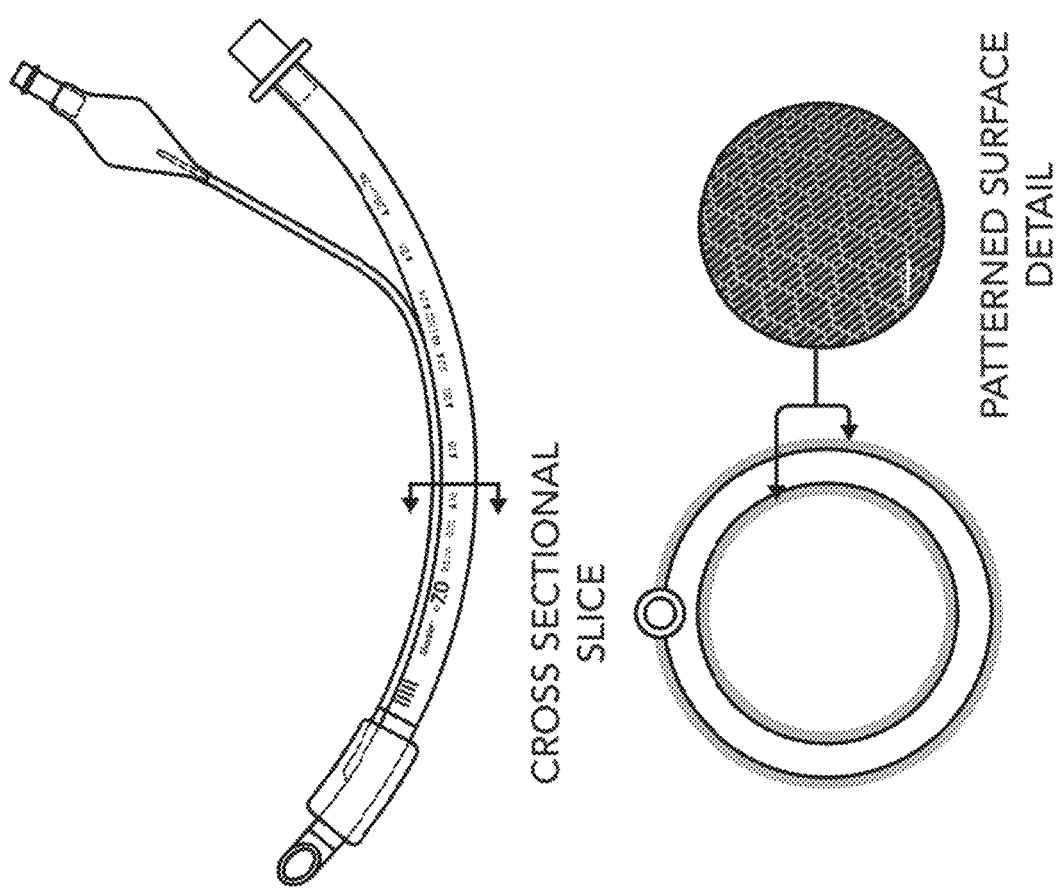
FIG. 8 depicts how the texturing can be disposed an inner surface of a medical device such as for example an endotracheal tube.
Figure 9:
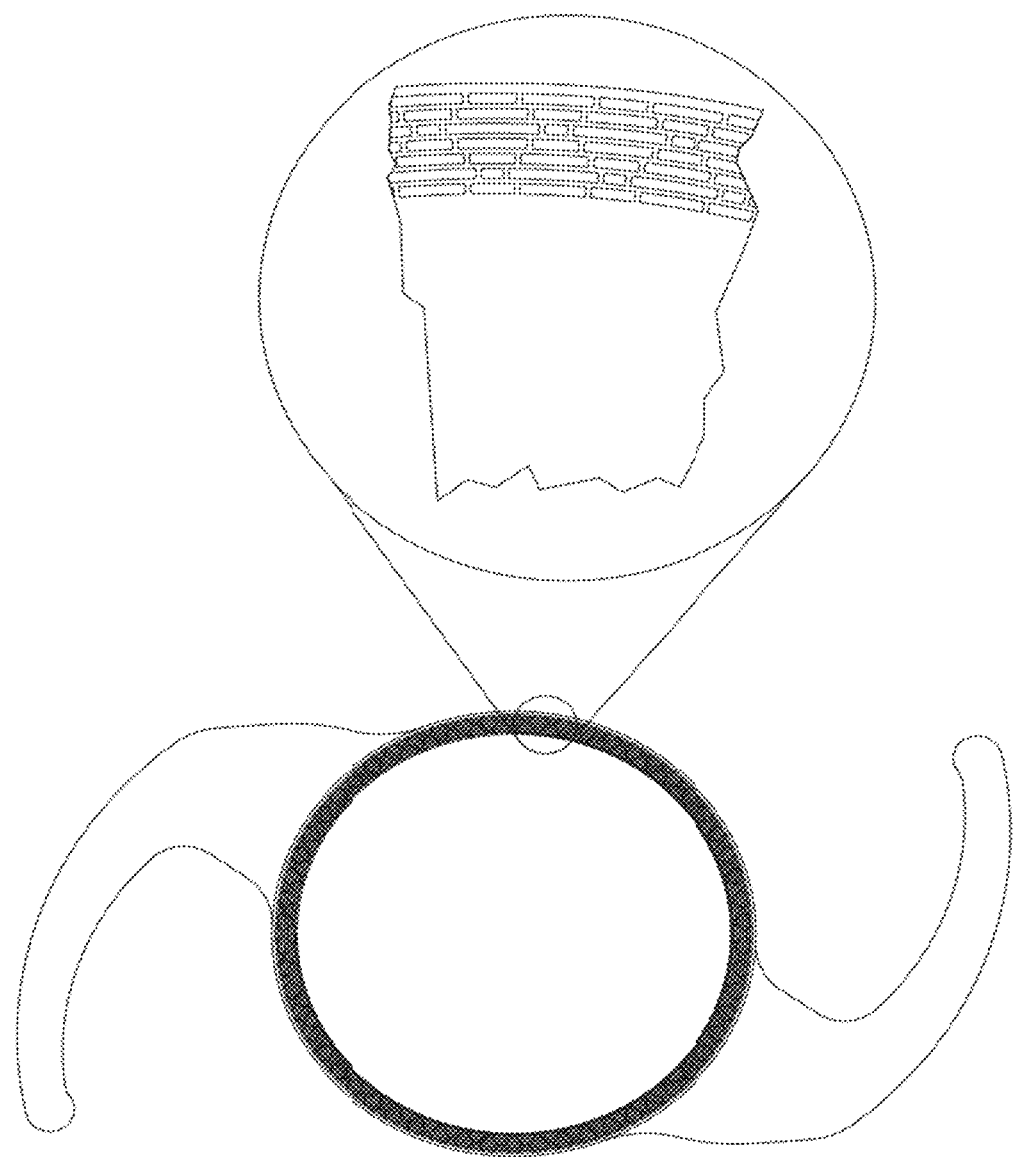
FIG. 9 depicts how the texturing can be disposed a surface of a medical device such as for example an intraocular lens.
Figure 11B:
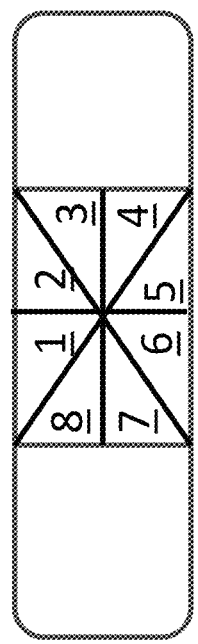
FIG. 11(B) depicts another exemplary embodiment of an article in which the grids 1-8 are arranged in a radial fashion.
Figure 11:
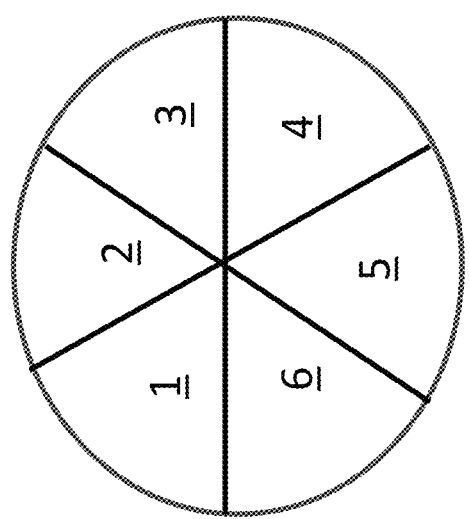
FIG. 11(A) depicts an exemplary embodiment of an article in which the grids 1-6 are arranged in a radial fashion.
FIG. 11(C) depicts an embodiment where fluid flow is directed radially away from the wound (i.e., the linear channels between elements of the pattern are arranged to direct the fluid radially outwards)
FIG. 11(D) depicts an embodiment where the fluid flow is directed in a circumferential direction away from the wound (the channels between elements are arranged such that the fluid would have to flow circumferentially away from the wound)
FIG. 11(E) depicts an embodiment where some segments permit fluid flow in the radial direction (i.e., the linear channels between elements of the pattern are arranged to direct the fluid radially outwards), while some segments prevent fluid flow in the radial direction ((i.e., the linear channels between elements of the pattern are arranged to be perpendicular to the direction of fluid flow and to prevent the fluid radially outwards)
FIG. 11(F) depicts texture that varies in size from one point to another.
FIG. 11(G) also depicts texture that varies in size from one point to another.
FIG. 11(H) depicts and embodiment where pattern density varies systematically from one point to another.

In one embodiment, the pattern can be disposed on tubular surfaces used in medical devices such as on the surface of a catheter or on the surface of an endotracheal tube. The pattern can be disposed on an inner surface and/or outer surface of the catheter or the endotracheal tube so as to prevent migration of cells in the catheter or the endotracheal tube, while permitting other fluids to flow through the catheter or endotracheal tube. FIG. 8 shows an exemplary endotracheal tube having a pattern disposed on an inner surface thereof. FIG. 8 also shows a cross-sectional slice of the endotracheal tube and an inset of the patterned surface in detail. The orientation of the patterns and the dimensions of the patterns can be adjusted based to control fluid flow. In one embodiment, the pattern can be disposed on an intraocular lens. FIG. 9 shows an intraocular lens with a pattern disposed thereon. FIG. 9 also shows an inset showing a detailed view of the pattern. FIGS. 10(A)-(E) show an exemplary intraocular lens having a pattern disposed on a surface thereof. FIG. 10(A) shows a side perspective view of the intraocular lens. FIG. 10(B) shows a top view of the intraocular lens. FIG. 10(C) shows a cross-section view of the intraocular lens. FIG. 10(D) shows a patterned surface on the posterior of the intraocular lens. FIG. 10(E) shows an inset of the patterned surface in detail. The orientation of the patterns and the dimensions of the patterns can be adjusted based to control fluid flow FIG. 11(A) depicts an exemplary embodiment of an article in which the grids 1-6 are arranged in a radial fashion. FIG. 11(B) depicts another exemplary embodiment of an article in which the grids 1-8 are arranged in a radial fashion. The texture in grid can be arranged such that the patterns proximate to the source of fluid flow allow for an easy passage of fluid away from the source or prevent easy passage of fluid flow from the source. Alternatively by choosing the texture and the orientation of the pattern, the fluid flow or the flow of particulate matter can be controlled. In another embodiment, the patterns need not be disposed in grids but can be oriented in a manner that permits control over fluid flow or particulate flow during the use of the article.

In one embodiment, the article of the FIGS. 11(A) and 11(B) can be a wound dressing that is applied to a wound where the center point of the wound dressing is disposed directly over the wound. FIGS. 11(C)-11(E) show embodiments where pattern orientation can be used to tailor fluid flow from a wound. It is assumed that the center point of the each of the wound dressings of the FIGS. 11(C)-11(E) is disposed directly over a wound. FIG. 11(C) depicts an embodiment, where fluid flow is directed radially away from the wound (i.e., the linear channels between elements of the pattern are arranged to direct the fluid radially outwards), while in the FIG. 11(D), the fluid flow is directed in a circumferential direction away from the wound (the channels between elements are arranged such that the fluid would have to flow circumferentially away from the wound). In the FIG. 11(E), some segments permit fluid flow in the radial direction (i.e., the linear channels between elements of the pattern are arranged to direct the fluid radially outwards), while some segments prevent fluid flow in the radial direction ((i.e., the linear channels between elements of the pattern are arranged to be perpendicular to the direction of fluid flow and to prevent the fluid radially outwards).

Figure 11F:
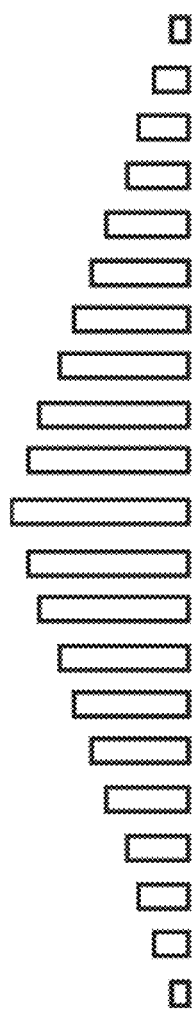
Figure 11G:
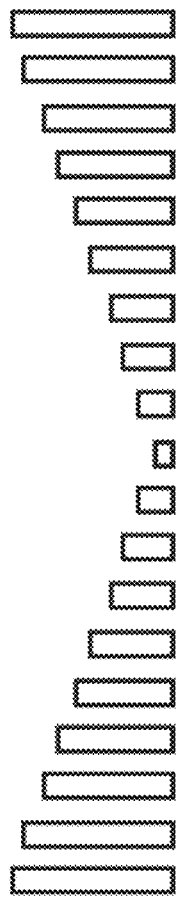
Figure 11:
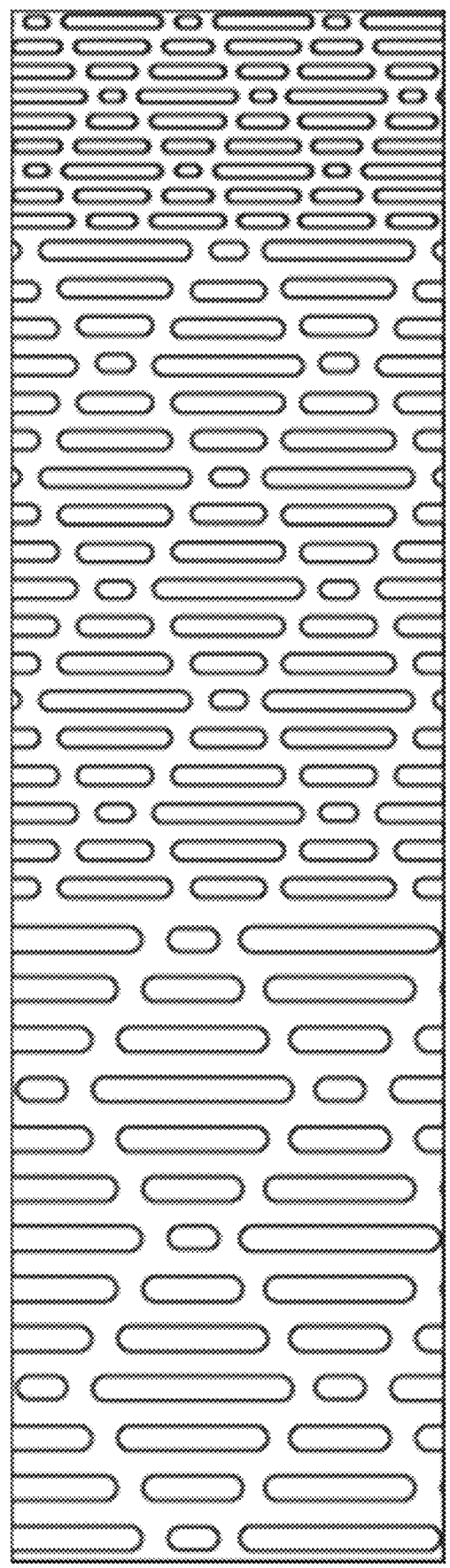

The height of the patterns can be systematically varied from the center to the edges of the wound dressing. FIGS. 11(F) and 11(G) are cross-sectional side views of a wound dressing where pattern thickness is varied from the center to the outer circumference. This is done to facilitate or to prevent fluid flow from a wound upon which the wound dressing is disposed. The wound dressing of the FIG. 11(F) would be utilized to arrange for the peak of the patterns to contact the wound-thus allowing for the fluid to travel rapidly to the outer radius of the wound dressing, while the wound dressing of the FIG. 11(G), is designed to allow fluid flow from the center but to be trapped at the periphery.

FIG. 11(H) details how the density of the patterns can be varied in a given direction to control fluid flow. In the FIG. 11(H), the density of the patterns is increased from left to right to vary the fluid flow.

Figure 12:
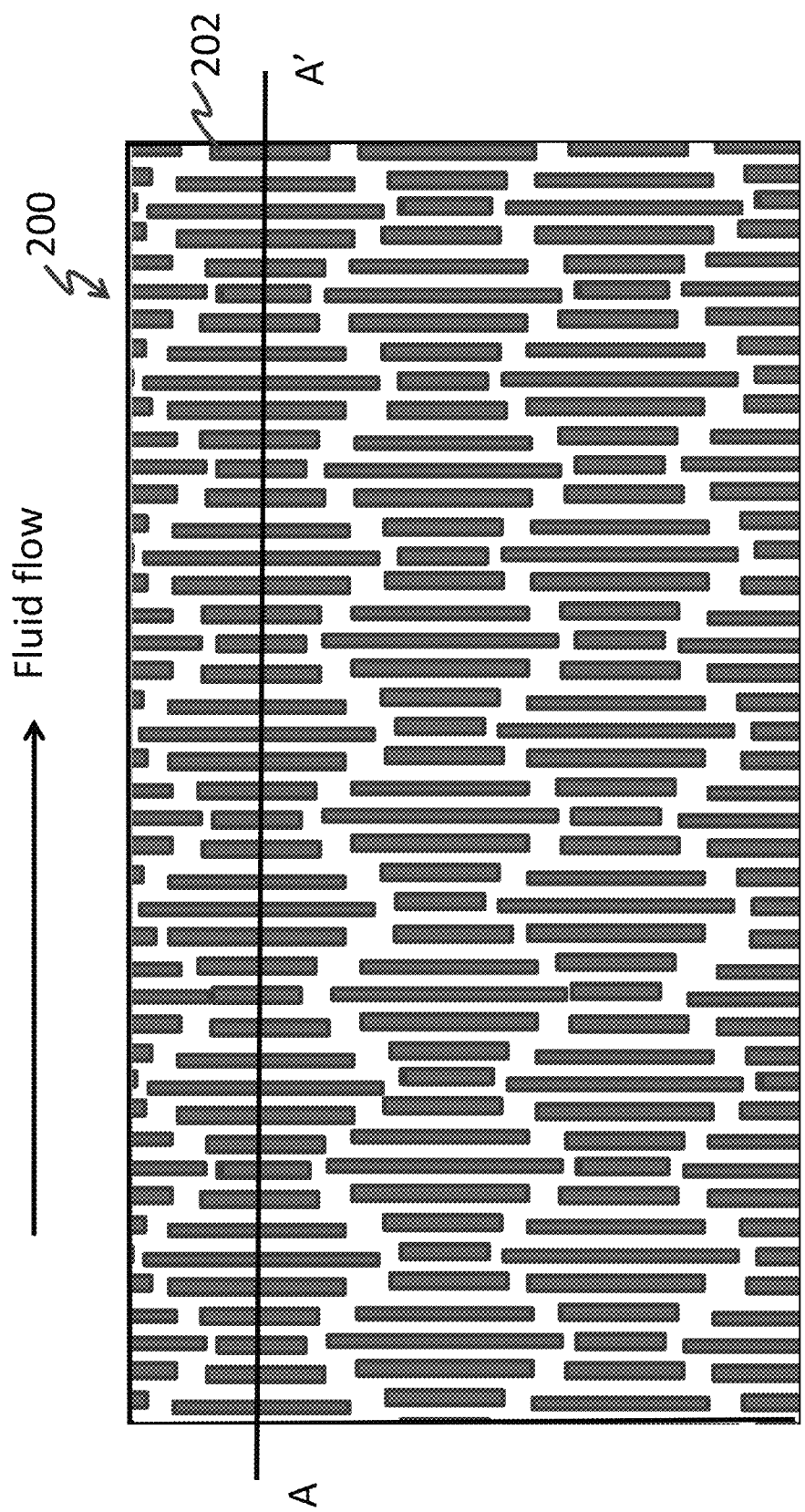
FIG. 12 depicts an embodiment where the elements of the pattern are perpendicular to the direction of flow.

FIG. 12 depicts one manner of orienting patterns in or on a conduit 200 to prevent the migration of bacterial cells or to hinder the flow of a fluid. As seen in the FIG. 12, the patterns can be arranged with their axes perpendicular to the flow direction. As shown in the FIG. 12, the elements of the pattern are arranged to provide maximum resistance to the flow of fluid and the contents contained therein. The arrangement of the patterns in this manner restricts the flow of fluid or of particulate matter (particles, cells and the like) to the tortuous path, while making it difficult for cells and/or the fluid to reach the other end of the conduit. In short, by reducing the area of the tortuous path while simultaneously increasing its length and while simultaneously increasing the number of elements in the path of the fluid, the particulate matter can be restricted from moving along the length of the conduit. Cellular matter contained in the fluids can be entrapped in the linear channels (as detailed above, the channels are linear when viewed in the second direction), while letting a fluid flow along the length of the conduit albeit slower than it would on a smooth surface.

Figure 13:
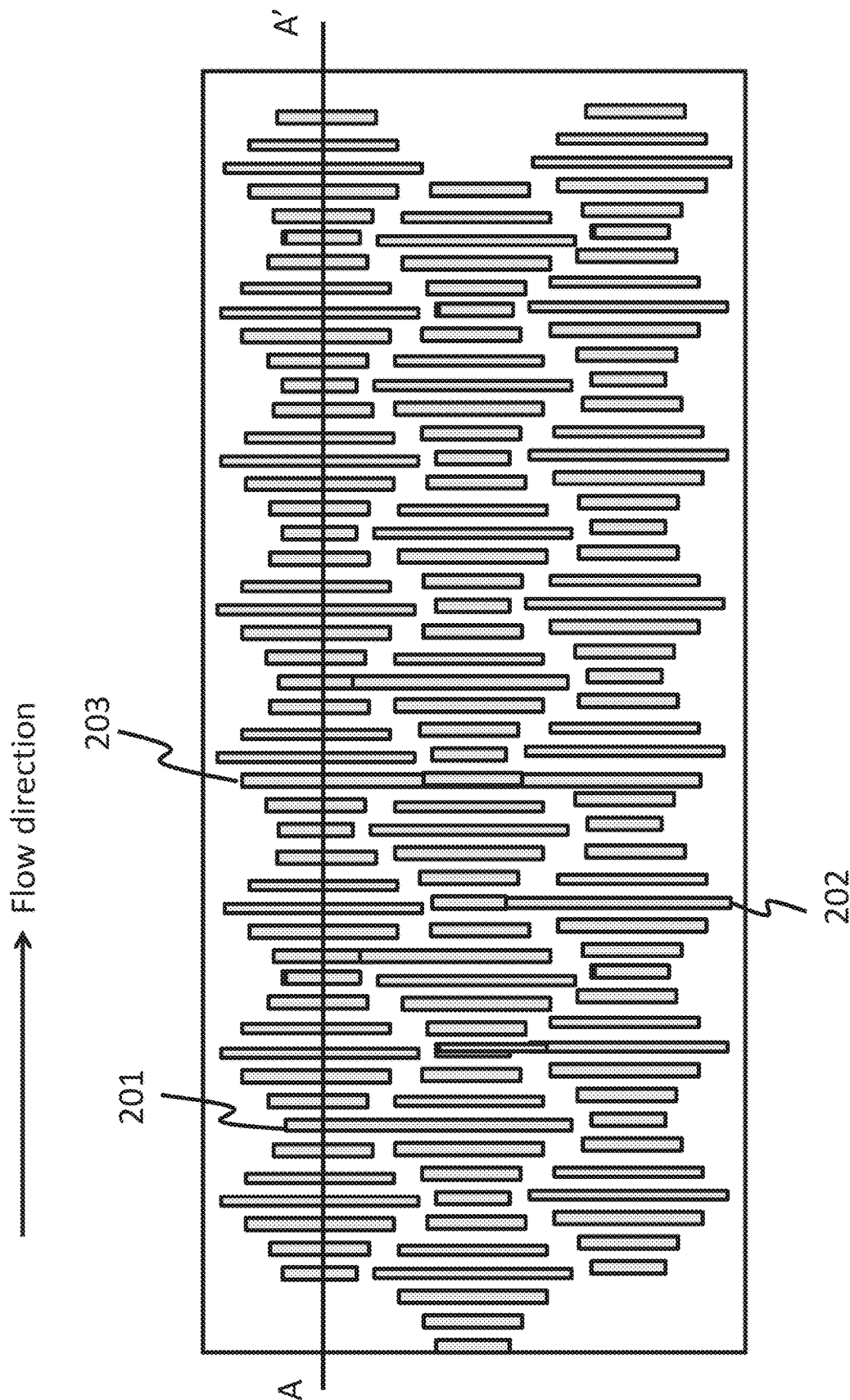
FIG. 13 depicts an embodiment where the elements of the pattern are inclined at an angle θ to the direction of flow.

The orientation of the axis of the patterns can be adjusted to increase or decrease the flow of the fluid or to increase or decrease the ability of the pattern to entrap migrating particulate matter. The FIG. 13 reflects patterns whose axes are oriented at an angle θ to the flow direction. The angle θ can be varied from 5 degrees to 175 degrees. By orienting the axis of the pattern as shown in the FIG. 13, the pattern will appear to be in the form of a helix on the surface of the conduit.

In one embodiment, sections of patterns can have their axes oriented from 5 degrees to 90 degrees, while other sections of patterns can have their axes oriented from 91 degrees to 175 degrees. This is detailed in the FIG. 1 above. By orienting different sections of the pattern at different angles, the rate of travel of particulate matter in the fluid can be controlled. The migration of bacterial cells, tissue cells, or the like can also be controlled by varying pattern orientation. By changing the orientation of the patterns on or in a conduit, patterns of fluid flow (e.g., vortices) that develop during fluid flow can be minimized.

Figure 14:
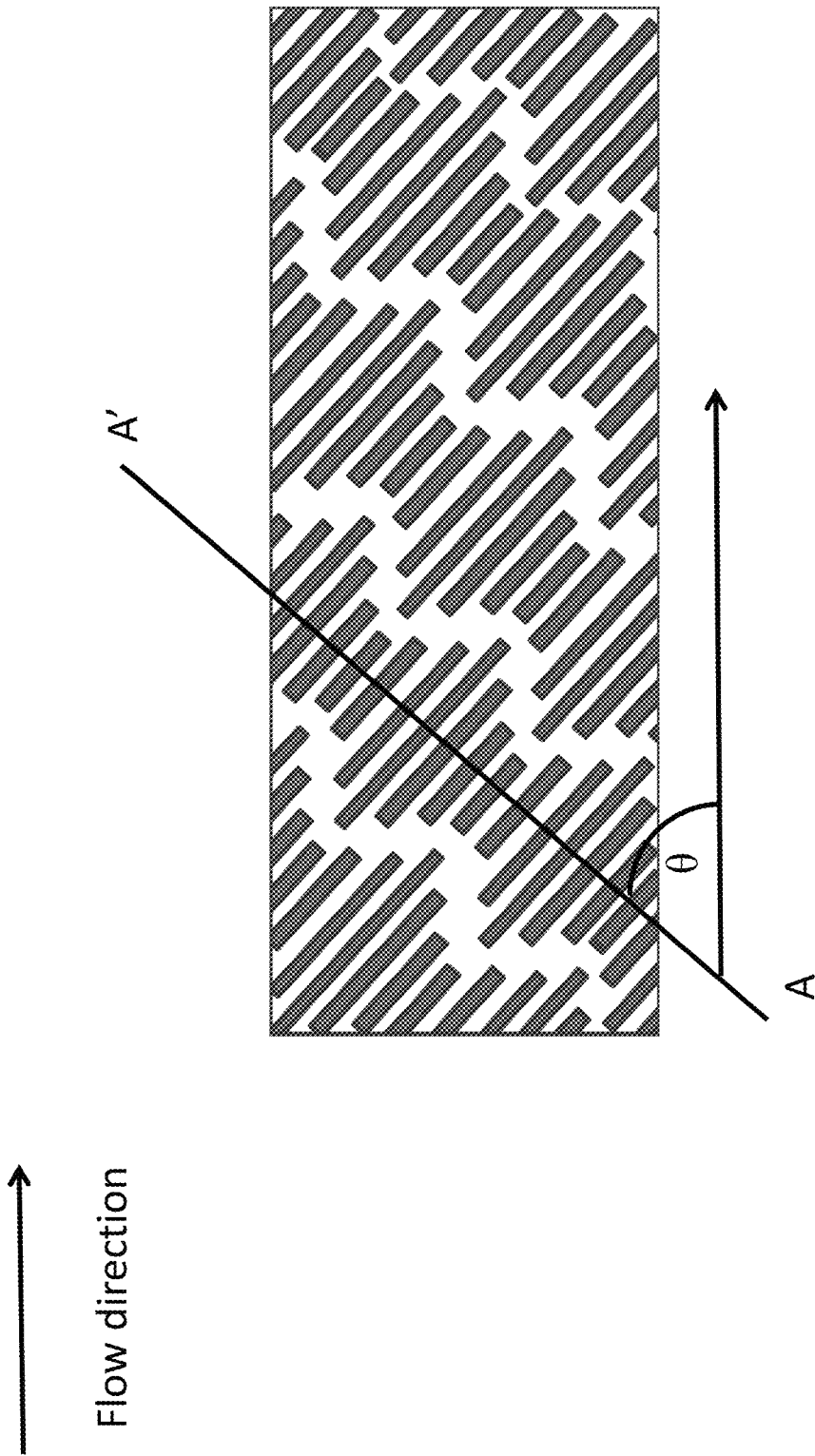
FIG. 14 depicts an embodiment where some elements of one set of patterns overlap with elements of a neighboring pattern.

In one embodiment, in one manner of increasing the length of the tortuous path that a fluid (or its particulate contents) has to traverse, the elements of some of the patterns can be conjoined with an element from a neighboring pattern. This is depicted in the FIG. 13, where elements 201, 202 and 203 are joined together with an element from a neighboring pattern to produce an elongated element. This modification can also be made on patterns whose axes are inclined to the flow direction, as shown in FIG. 14. By increasing the aspect ratio of an element in one pattern with respect to that of a neighboring pattern the length of the tortuous path can be increased and its volume can be increased.

The elements that are joined together can be periodic or aperiodic. In one embodiment, a particular element (e.g., every $3^{rd}$ element from the left of each pattern) is extended to contact its counterpart in at least one neighboring pattern thus producing a periodic disruption to the flow passages or pathways. The extended element can contact one or more neighboring elements.

In another embodiment, random elements from one pattern can be extended to contact one of more elements on neighboring patterns resulting in an aperiodic disruption to the flow passages or pathways.

Figure 15A:
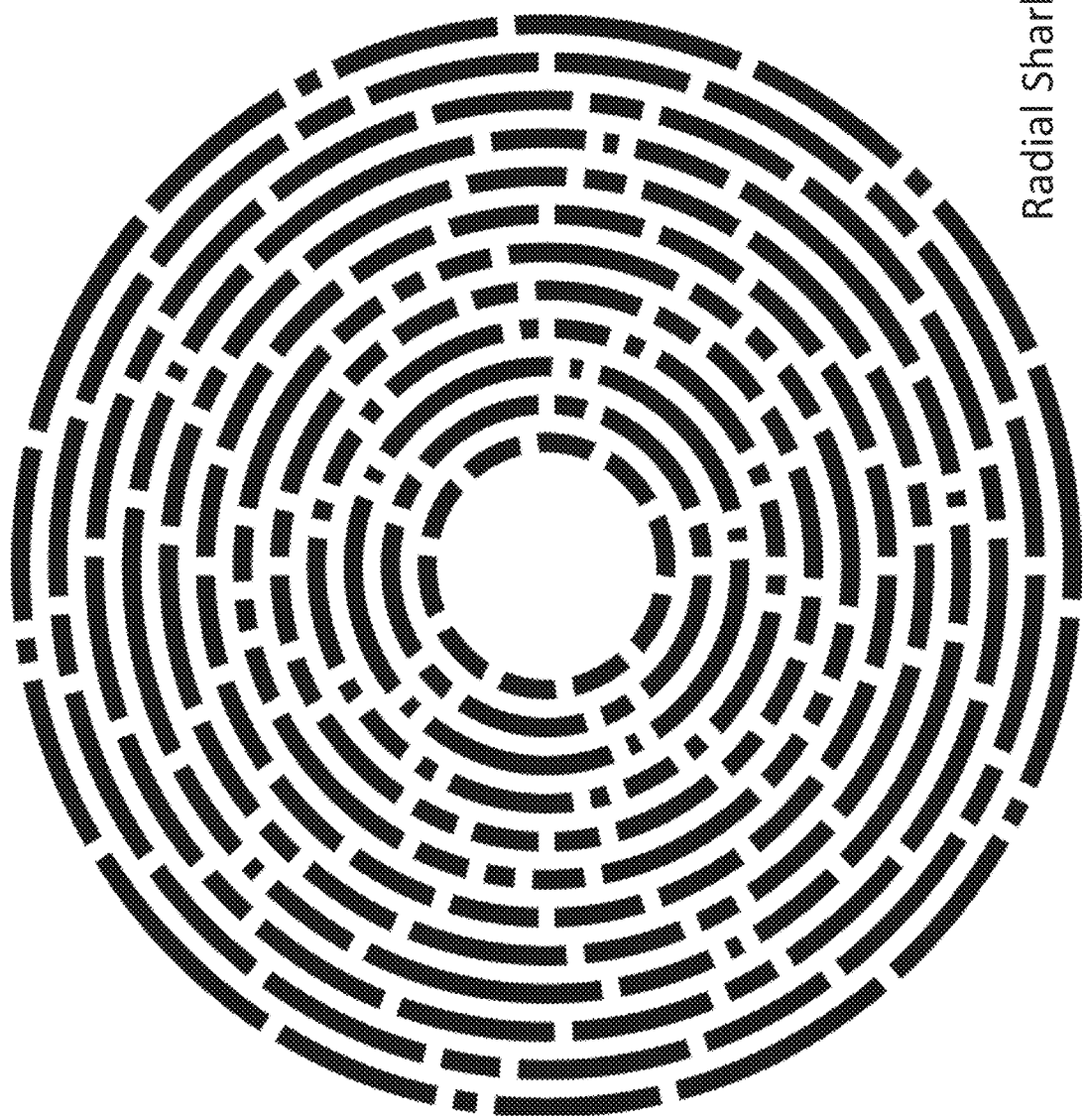
FIG. 15(A) depicts an embodiment where the elements of the pattern are arranged in a circumferential direction.
Figure 15B:
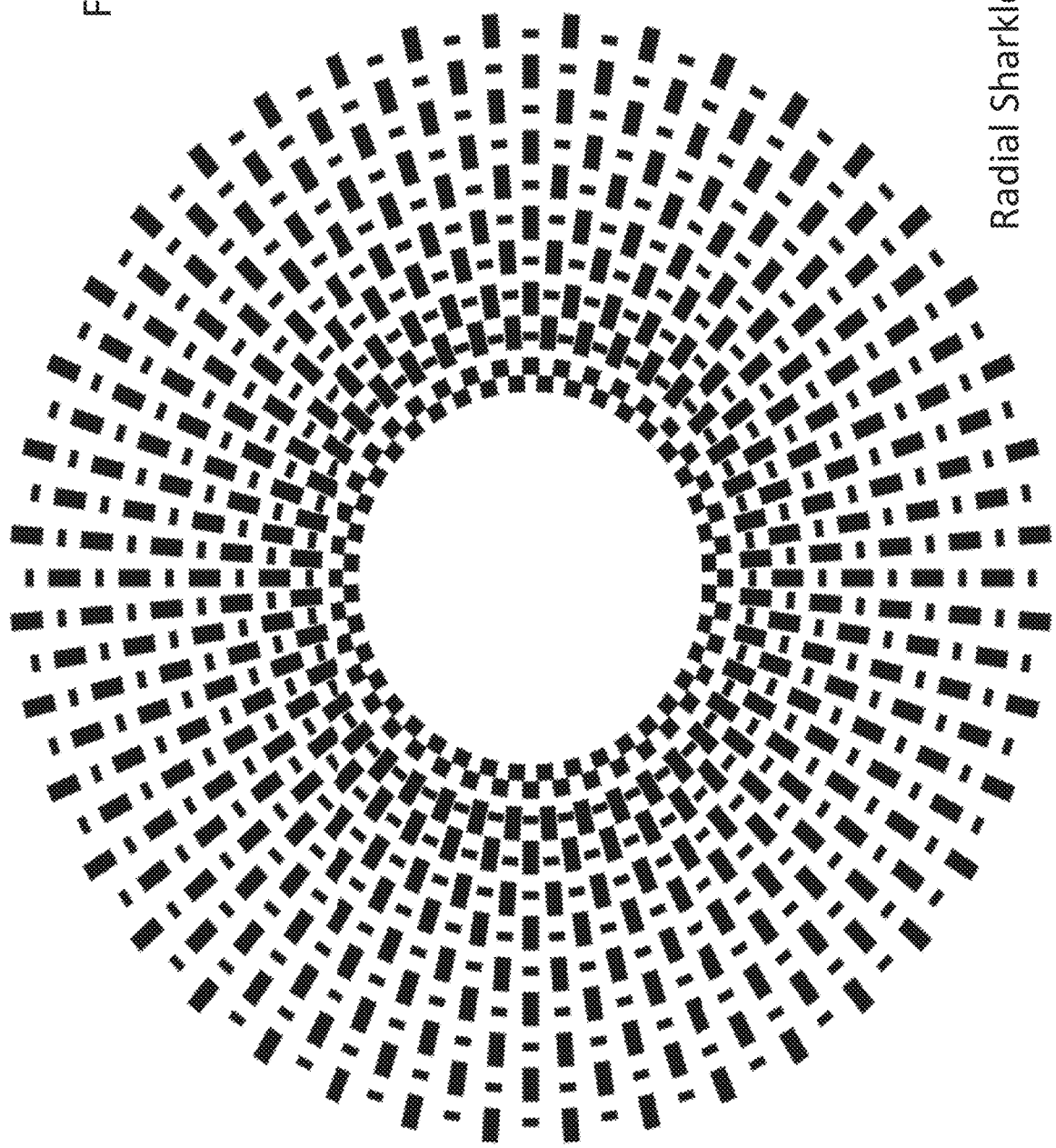
FIG. 15(B) depicts an embodiment where the elements of the pattern are arranged in a radial direction.

FIG. 15(A) depicts one embodiment where the elements of the pattern are arranged to be parallel with one another in the circumferential direction. In other words the elements of the pattern are concentric about the center point of the pattern. FIG. 15(B) depicts an embodiment where the elements of the pattern are arranged in a radial direction. These patterns can be used to control the flow of fluids from the center of the texture to the outer circumference.

In one embodiment, the elements of the pattern are arranged to be parallel with one another in the circumferential direction along an inner surface of a conduit such that the spacing of element relative to one another forms a continuous pattern along the circumference of the inner surface. In another embodiment, the elements of the pattern are arranged to be parallel with one another in the circumferential direction along an inner surface of a conduit such that the spacing of each element relative to one another forms a discontinuous pattern along the circumference of the inner surface with gaps in between groupings of elements. Any number of elements may be grouped together in between the gaps, e.g., 3, 5 or 7 elements. In addition to controlling fluid flow and/or cell migration, the pattern may also be used to control airflow or mixing, e.g., a fuel mixture.

As noted above, the use of pattern orientation can be used to control flow from one end of a conduit to another. The patterns and the methods described herein are exemplified by the following non-limiting examples.

EXAMPLES

Example 1

In one experiment, smooth (SM) and micropatterned samples were fabricated by casting biomedical grade polydimethylsiloxane elastomer (Silastic® MDX4-4210, Dow Corning; PDMSe) against negative silicon wafer molds. Circular samples (d=20 mm) were adhered to a 12-well plate with features aligned perpendicular to the direction of cell migration and treated with fibronectin (15 μg/mL overnight) to facilitate cell attachment. SM PDMSe rectangles (3 mm×20 mm) were placed along the center of the sample to create a modified scratch assay. Human lens epithelial cells (HLECs) were seeded over the entire configuration at $1×10^4$ cells/cm² and maintained in growth media (Eagle's minimum essential media, 20% fetal bovine serum, 50 U/ml penicillin/streptomyocin and 1 µg/ml Fungizone antimycotic). At ~70% confluence, PDMSe rectangles were removed to allow cell migration across the empty patterned area. Migration was monitored via light microscopy until Day 7 when samples were stained with CellTracker Orange and fixed. Fluorescent microscopy images were taken of the wounded area and the average area covered by cells within this region was calculated using ImageJ software.

Figure 16:
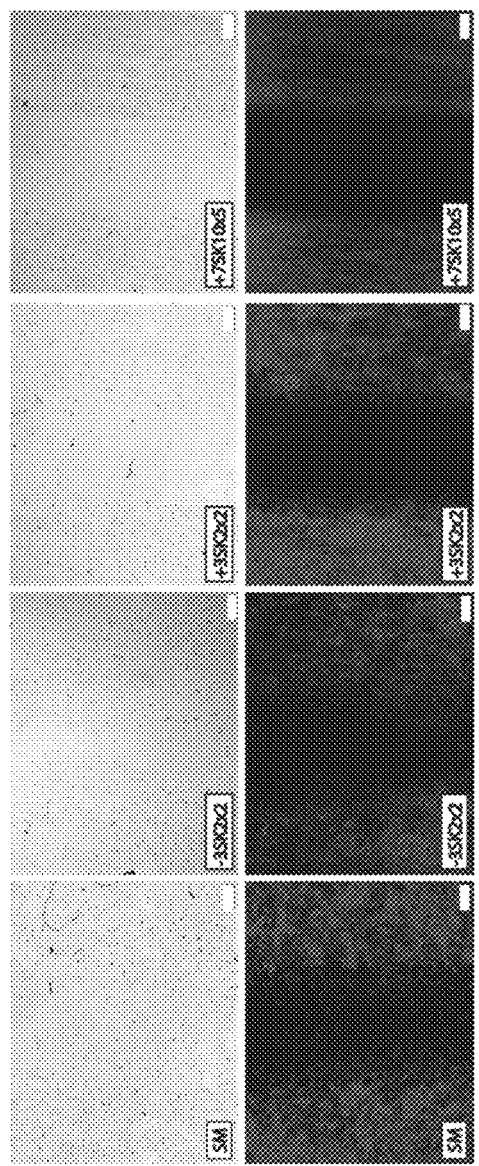
FIG. 16 shows representative fluorescent images of cells stained with Cell Tracker (red) on PDMSe samples at the migration assay endpoint (7d) for the Example 1.
Figure 17:
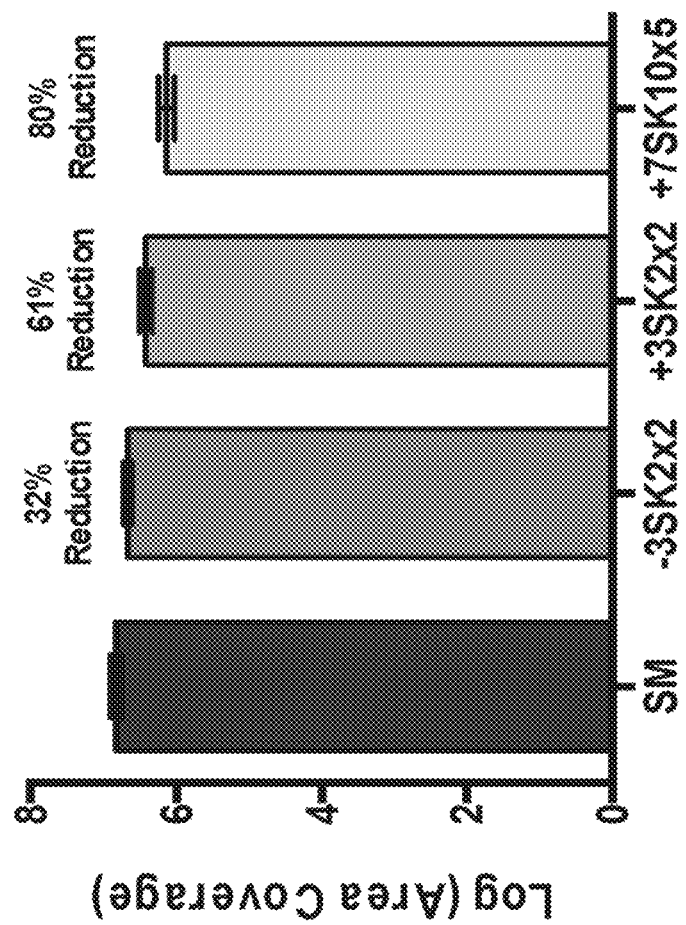
FIG. 17 shows average log(area coverage) of wounded area in migration assays at the 7 day time point for the Example 1.

All patterns significantly reduced HLEC migration compared to smooth surfaces (FIG. 16, FIG. 17, Table 1). FIG. 10 shows representative fluorescent images of cells stained with CellTracker (red) on PDMSe samples at the migration assay endpoint (7d). FIG. 17 shows average log (area coverage) of wounded area in migration assays at the 7 day time point. All topographies significantly reduced HLEC migration compared to smooth with the highest reduction on the +7SK10×5 surface. Error bars represent 95% confidence intervals.

(Scale bars, 500 µm)

Each pattern grouped separately in a Tukey Test for multiple comparisons (Grouping, Table 1) indicating that all patterns had significantly different levels of performance. The best performing surface, +7SK10×5, reduced HLEC coverage in the wounded area by 80%, p=0.0001. The +7SK10×5 pattern has been selected for prototype production for animal studies. The +7SK10×5 topography will be tiled in a checkerboard pattern (FIG. 18) to create a surface that blocks HLEC migration from all directions and this layout will be used to create prototypes for animal studies.

Table 1 is a summary of log reduction (LR) data analysis versus smooth.

TABLE 1

| Pattern | n | Mean LR | Mean PR | p value | Grouping |
| --- | --- | --- | --- | --- | --- |
| +3SK2x2 | 3 | 0.41 | 61% | 0.002 | A |
| −3SK2x2 | 3 | 0.17 | 32% | 0.019 | B |
| +7SK10x5 | 3 | 0.70 | 80% | 0.0001 | C |

The best performing topography (+7SK10×5) was translated into a checkerboard pattern, to inhibit cell migration from all directions.

Example 2

This example was conducted to demonstrate the wound healing capabilities of the patterns. Smooth (SM) and micropatterned (+1.5SK10×2 and +10SK50×50) samples were fabricated by casting polydimethylsiloxane elastomer (Xiameter RTV-4232-T2, Dow Corning; PDMSe) against negative silicon wafer molds. Circular samples (d=20 mm) were adhered to a 12-well plate with features aligned parallel to the direction of cell migration and treated with fibronectin (15 µg/mL overnight) to facilitate cell attachment. SM PDMSe rectangles (5 mm×20 mm) were placed along the center of the sample to create a modified scratch assay. Human epidermal keratinocytes (HEKs) were seeded over the entire configuration at 1×10$^4$ cells/cm$^2$ and maintained in complete keratinocyte growth media (dermal cell basal medium, 0.4% bovine pituitary extract, 0.5 ng/ml rh TGF-alpha, 6 mM L-glutamine, 100 ng/ml hydrocortisone, 5 µg/ml insulin, 1 µM epinephrine, 5 µg/ml apo-transferrin, 50 U/ml penicillin/streptomyocin and 1 µg/ml Fungizone antimycotic). At ~70% confluence, PDMSe rectangles were removed to allow cell migration across the empty patterned area. Migration was monitored via light microscopy until Day 4 when samples were stained with CellTracker Orange and fixed. Fluorescent microscopy images were taken of the wounded area and the average area covered by cells within this region was calculated using Image J software.

Figure 18:
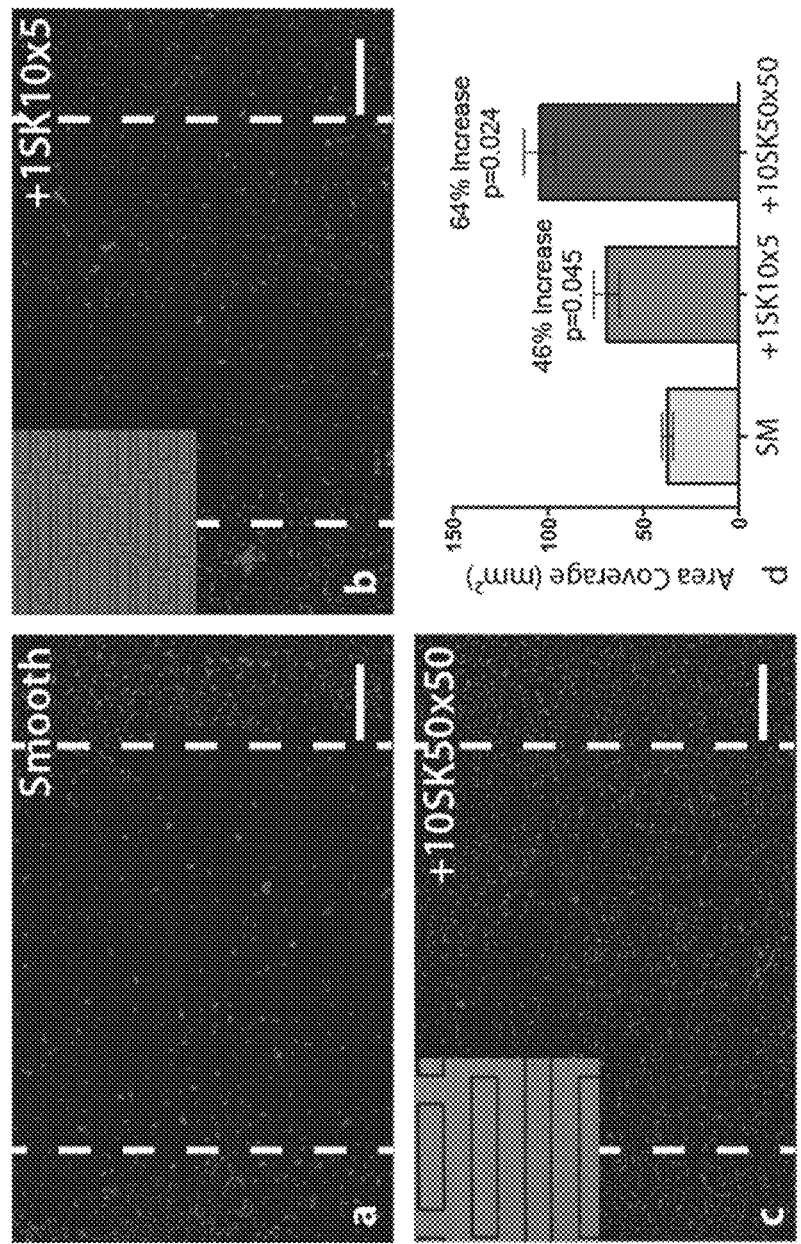
FIG. 18 shows representative fluorescent images of cells stained with CellTracker (red) on PDMSe a) Smooth and b) Sharklet samples at the migration assay endpoint (7d)

Results indicate that this micro-pattern induced highly oriented migration of human epidermal keratinocytes (HEK) on fibronectin-coated polydimethysiloxane elastomer (PDMSe) surfaces that led to 46% and 64% faster closure of a modified scratch wound in vitro versus SM when features were oriented in the direction parallel to cell migration. FIG. 18 shows representative fluorescent images of cells stained with CellTracker (red) on PDMSe a) Smooth and b) Sharklet samples at the migration assay endpoint (4d). Scale bars, 500 µm. C) Quantification of the average area covered showed 46% and 64% increases in artificial wound closure on the +1.5SK10×5 and +10SK50×50 patterns, respectively. Without being limited to theory it is believed that a topographic design that reduces feature size radially toward the center of the pattern with features oriented radially would further enhance this effect.

Example 3

In this example, the pattern is disposed on the inside of a tube to determine its effect on fluid flow. The axis of the pattern is oriented to be perpendicular to the fluid flow while the linear channels between adjacent elements are oriented to be parallel to the fluid flow. The linear channels between adjacent elements will be oriented parallel to the long axis of the tube and parallel to the direction of flow. As will be seen from the results, this orientation reduces accumulation of biological fluids (e.g., mucus) and the formation of microbial biofilms.

The disclosed patterns reduce microbial biofilm formation in the presence of flow on biological fluid contacting devices (e.g., endotracheal tube (ETT), central venous catheter (CVC)) when oriented parallel to the direction of flow. It is not desirable to form a biofilm on the surface of the catheter or on the surface of the endotracheal tube.

Inoculated media is pumped over thermoplastic polyurethane (TPU) Sharklet test and unpatterned control surfaces at a 25° decline. Log reduction boxplot of colony forming units was generated from quantifying test and control surface biofilms with or without media containing mucin (See FIG. 19(A)). Example images are of *P. aeruginosa* biofilm on control and test surfaces grown in (tryptic soy broth) TSB+mucin condition demonstrate that larger biofilms were formed on smooth surfaces as compared with textured surfaces. Orientation of the micro-pattern along the direction of flow results in less TSB growth media on the Sharklet surface compared to an unpatterned surface. Details are provided below. Similarly, when artificial mucus is dripped down surfaces at a 25° decline the fluid maintains a narrower path compared to the same fluid dripped down a smooth surface. Therefore overall surface interaction with fluid on a Sharklet micro-patterned surface is reduced compare to a smooth surface.

A drip flow biofilm reactor is used following manufacturer's instructions and variations included below to compare each thermoplastic polyurethane (TPU) Sharklet micropattern and smooth TPU surface for biofilm accumulation. Test patterns are evaluated after being exposed to 200 milliliter (ml) of *P. aeruginosa* bifA- or *S. aureus*-inoculated TSB with and without 2 microgram/milliliter mucin dripped across the surface for 48-96 hours at room temperature in a closed recirculating flow system. To establish growth of *S. aureus* biofilms the 200 ml of growth media was replaced approximately every 12 hours. The biofilms are quantified by colony forming unit/milliliter (CFU/ml) and crystal violet biomass staining (log (optical density)). The log transformed data for each pattern and quantification method is subtracted from the log transformed smooth data for each quantification method. This generates a log reduction (LR) value which is evaluated using a general linear model ANOVA and a single paired t-test. The least squared mean LR, corresponding median percent reduction, t-test derived p-value and Tukey grouping are determined for each test pattern in each condition tested.

Performance reducing microbial biofilm is presented in percent reduction from an unpatterned surface and the percent reductions were fit into statistical groupings using General Linear Model ANOVA and Tukey comparison. The results are shown in the Table 2. Additionally, the log reductions of both *P. aeruginosa* bifA and *S. aureus* on −3SK-NT2×2 are shown in FIG. 13(A). Examples of *P. aeruginosa* bifA biofilm reduction on Sharklet micro-patterned TPU compared to smooth TPU are seen in the FIGS. 19(B) and 19(C). The controlled and narrowed nature of growth media (FIG. 19(D)) or artificial mucus (FIG. 19(E)) flow down Sharklet micro-patterned surface (FIG. 19(D)) compared to smooth surface is evident. Biological fluids interact overall less with the Sharklet micro-patterned surface than they do with smooth surfaces.

TABLE 2

| Pattern type | Pattern Orientation | % Reduction | p-value | Tukey Grouping |
| --- | --- | --- | --- | --- |
| 3 SK-NT 2x2 | Parallel | 96% | 0.014 | A |
| −3 SK-NT 2x2 | Parallel | 92% | 0.036 | A |
| −3 SK-T 2x2 | Parallel | 72% | 0.116 | AB |
| −3 SK-NT 2x2 | Perpendicular | 72% | 0.109 | AB |
| 3 SK-T 2x2 | Parallel | 65% | 0.116 | AB |
| 7.3 SK-NT 10x5 | Parallel | 57% | 0.106 | AB |
| 11.3 SK-NT 20x5 | Parallel | 55% | 0.146 | AB |
| 8.7 SK-NT 10x2 | Parallel | 37% | 0.059 | AB |
| 2.6 SK-NT 10x2 | Parallel | 23% | 0.25 | AB |
| 3 SK-NT 2x2 | Perpendicular | −88% | 0.993 | B |

Example 4

The patterns disclosed herein enhances fluid flow on a biological fluid contacting device (e.g. ETT) when oriented parallel to the direction of flow. For example, to assess mucus flow over the Sharklet micro-topography in the presence of gravitational force and forced air flow, smooth (SM) and micro-patterned samples made in thermoplastic polyurethane (Tecoflex EG85A, Lubrizol; TPU) rectangular samples (h=5 cm; w=2 cm) with Sharklet features aligned perpendicular or parallel to the length of the sample were adhered to a glass plate held at a 30° angle. A plastic tube (ID=7 mm) was fixed at the top of the film and connected to a Siemens 900c Ventilator set to deliver 4-6 L of air over 20 breaths each minute. A 20-40 μL drop of artificial mucus (8% mucin, 4% lecithin, and 0.8% DNA) was placed at the opening of the ventilator tube and the distance (cm) and time (seconds), up to 120 seconds, required for the mucus to travel the length of the film was recorded. Three smooth and three patterned surfaces (per orientation) were tested in each experiment and the average rate (cm/sec) of flow over the three samples per surface type was calculated and compared. Each experiment was completed in triplicate.

In each experiment, the rate change on patterned surfaces is calculated as a percent difference from an unpatterned surface. Across all experiments, the percent rate change in mucus travel were statistically compared across patterned surfaces using a single t-test, General Linear Model ANOVA, and Tukey comparison. Most patterns increased the rate of mucus flow when oriented in the parallel direction (Table 4). Specifically, the large-dimension patterns (e.g. 10×5, 20×5, and 10×2) oriented in the parallel direction performed significantly better than all patterns oriented in the perpendicular direction based on Tukey grouping test (Table 4). Directionality specifically influenced the performance of individual pattern types. For example, the 2.6 SK-NT 10×2 Sharklet pattern with features in a parallel orientation significantly enhanced the rate of mucus flow by 75% (p=0.015) when compared to SM, in contrast to a reduced rate of mucus flow of −74% (p=0.141) with the same pattern but opposite orientation, i.e. features perpendicular to direction of flow (Table 4).

TABLE 4

| Pattern type | Pattern Orientation | % Rate Change | p-value | Tukey Grouping |
| --- | --- | --- | --- | --- |
| 7.3 SK-NT 10x5 | Parallel | 90% | 0.001 | A |
| 11.3 SK-NT 20x5 | Parallel | 90% | <0.001 | A |
| 8.7 SK-NT 10x2 | Parallel | 88% | 0.001 | A |
| 2.6 SK-NT 10x2 | Parallel | 75% | 0.015 | ABCD |
| 3 SK-T 2x2 | Parallel | 71% | 0.015 | ABCD |
| 4.8 SK-NT 10x2 | Parallel | 67% | 0.01 | ABCDE |
| −3 SK-NT 2x2 | Parallel | 58% | 0.018 | ABCDE |
| 3 SK-NT 2x2 | Parallel | 47% | 0.037 | ABCDEF |
| −3 SK-T 2x2 | Parallel | −10% | 0.958 | CDEFG |
| 3 SK-NT 2x2 | Perpendicular | −31% | 0.065 | EFG |
| 2.6 SK-NT 10x2 | Perpendicular | −74% | 0.141 | FG |
| 3 SK-T 2x2 | Perpendicular | −75% | 0.152 | FG |
| −3 SK-NT 2x2 | Perpendicular | −76% | 0.135 | G |

Example 5

Figure 20:
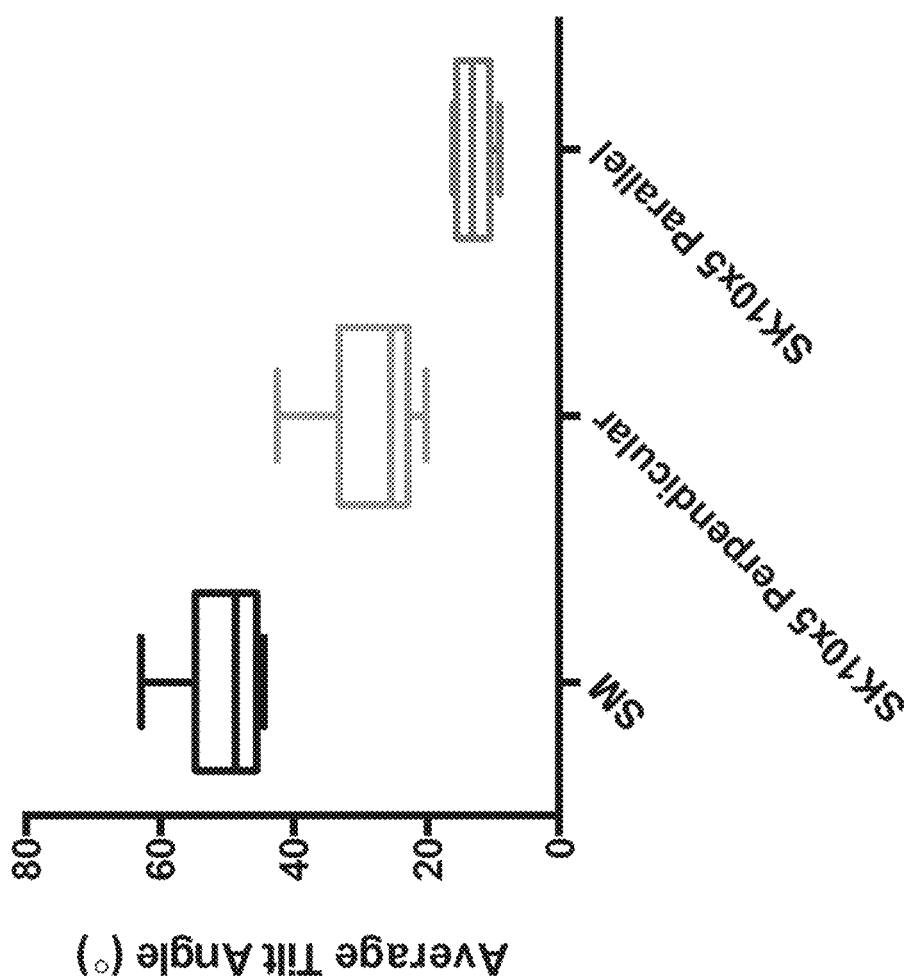
FIG. 20 shows a boxplot of slip angle data and graphically represents the spread in the data collected.

Tilt angles with simulated mucus (20 μL) were measured on samples replicated in thermoplastic polyurethane (TPU; Tecoflex EG70A, Lubrizol Corporation) tilted at 0.5°/s using a goniometer with an automated stage (Rame-hart Model 250 F4 Series Standard Goniometer). Micro-topographic features were aligned parallel and perpendicular to the direction of tilt. Three experiments were performed where three individual drops were measured on each sample at each orientation. Results were compared using ANOVA and Tukey Test ($\alpha=0.05$) and are shown in Table 5 and FIG. 20. FIG. 20 shows a boxplot of slip angle data and graphically represents the spread in the data collected. Table 5 shows average slip angle measurements.

TABLE 5

| Specimen | θ (°) | Tukey Grouping |
| --- | --- | --- |
| SK10x5‖ | 13 | A |
| SK10x5+ | 28 | B |
| SM | 50 | C |

Example 6

Figure 21A:
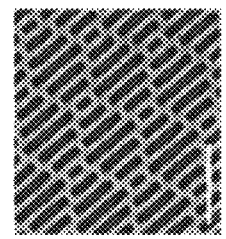
FIG. 21(A) depicts a Smooth (SM) surface.
Figure 21B:
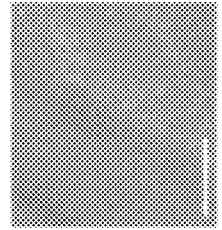
FIG. 21(B) depicts a Sharklet (SK) surface.
Figure 21C:
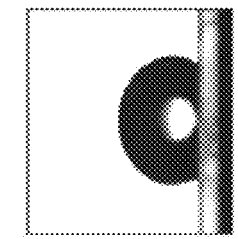
FIG. 21(C) depicts a droplet of fluid on the Smooth (SM) surface.
Figure 21D:
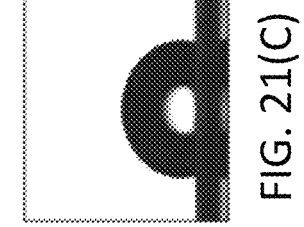
FIG. 21(D) depicts a droplet of fluid on the Sharklet (SK) surface shows the advancing contact angle in degrees of the Smooth (SM) and Sharklet (SK) surfaces, respectively.
Figure 21E:
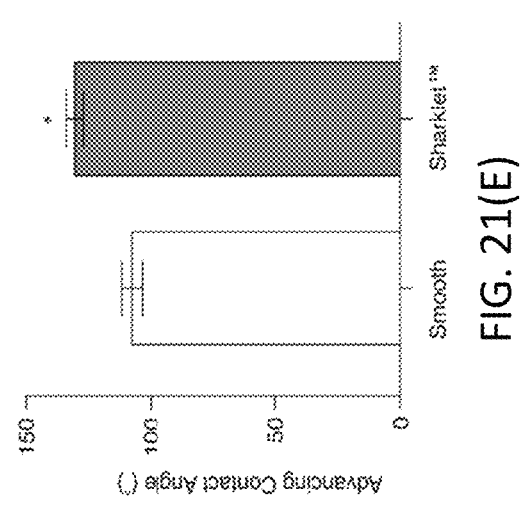
FIG. 21(E) is a graph depicting the results of the advancing contact angle in degrees for the smooth and textured surfaces.

This example was conducted to demonstrate the contact angle of fluid on Smooth (SM) and micropatterened (SK) surfaces replicated in thermoplastic polyurethane (Pellethane® 2363-90AE available from Lubrizol Corporation), as shown in FIGS. 21(A) and (B), respectively. Advancing contact angle was measured as an indication of surface hydrophobicity according to a protocol adapted from ASTM D7334-08. Samples of SM and Sharklet™ film were loaded onto a goniometer with a tilting base (Model 250 F4 Series Standard Goniometer, available from Rame-Hart Co. in Succasunna, N.J.) with the micropattern features aligned parallel to the direction of tilt. Drops of deionized water (10 µl) were placed on SM and Sharklet™ samples, the stage was tilted to 30° and advancing contact angles were measured using DROPimage™ Advanced Software (available from Rame-Hart Co. in Succasunna, N.J.). Three experiments were performed in which individual drops were measured on three replicates of each test surface. As shown in FIG. 21(D), fluid on the SK surface exhibits a significantly improved contact angle in comparison to the SM surface, which is shown in FIG. 21(C). The results of the advancing contact angle in degrees for the SM and SK surfaces are plotted in a graph shown in FIG. 21(E). As may be seen from FIG. 21(E), the advancing contact angle is about 20 degrees higher for the SK surface than the SM surface.

Example 7

Figure 22:
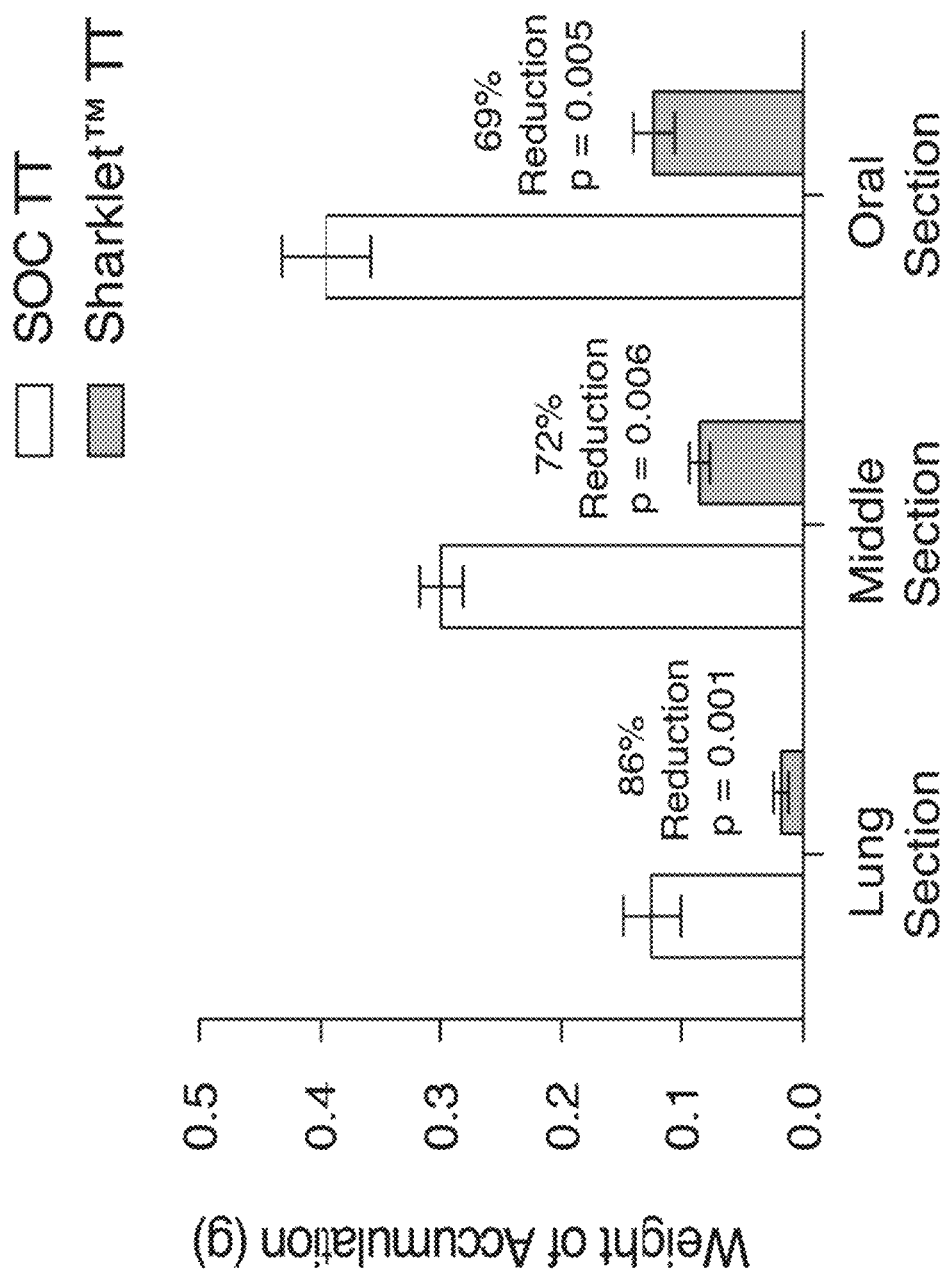
FIG. 22 shows the weight accumulation in grams of accumulated materials on an standard of care (SOC) endotracheal tube having a Smooth (SM) surface and an endotracheal tube having the Sharklet pattern disposed thereon.

This example was conducted to demonstrate the accumulation of material in different sections of endotracheal tubes used in a sheep. The endotracheal tubes have a Smooth (SM) or a micropatterened (SK) surface disposed thereon. The weight of accumulation in grams was measured for the lung section, middle section and oral section of each of the endotracheal tubes. The results are shown in FIG. 22. As may be seen from FIG. 22, the SK surface exhibited an 86% reduction in accumulated material in the lung section compared to the SM surface (with an error of uncertainty of p=0.001). For the middle section, the SK surface exhibited a 72% reduction in accumulated material relative to the SM surface (with an error of uncertainty of p=0.006). In the oral section, the SK surface exhibited a 69% reduction in accumulated material relative to the SM surface (with an error of uncertainty of p=0.005).

Example 8

Figure 23A:
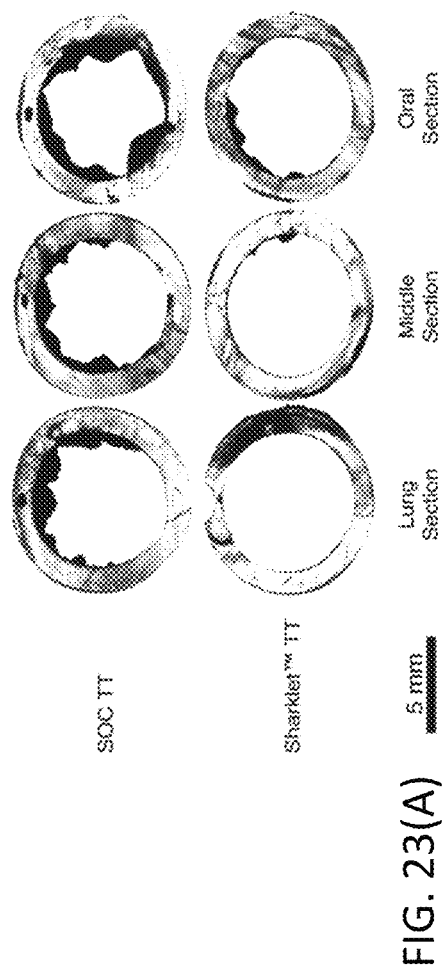
FIG. 23(A) shows photographs of accumulated materials in the lung, core and oral sections of endotracheal tubes having a Smooth (SOC) surface or a Sharlet (SK) surface disposed thereon.
Figure 23B:
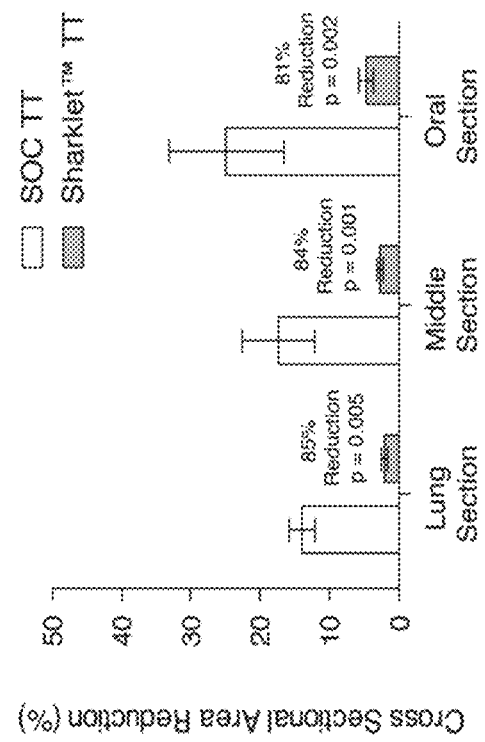
FIG. 23(B) shows the percentage of cross-sectional area reduction in the lung, middle and oral sections of endotracheal tubes having a Smooth (SOC) surface or a Sharlet (SK) surface disposed thereon.

This example was conducted to demonstrate the cross sectional area reduction in percent of the accumulated materials in different sections of endotracheal tubes used in a sheep. The endotracheal tubes have a Smooth (SM) or a micropatterened (SK) surface disposed thereon. The relative amounts of accumulated materials in the lung section, middle section and oral section of each of the endotracheal tubes having a SK or SM surface disposed thereon are shown in the photographs in FIG. 23(A). The reduction in the weight of accumulated material was measured for the lung section, middle section and oral section of each of the endotracheal tubes and the results were plotted in a graph shown in FIG. 23(B). The results show that the SK surface exhibited an 85% reduction in accumulated material in the lung section compared to the SM surface (with an error of uncertainty of p=0.005). For the middle section, the SK surface exhibited a 84% reduction in accumulated material relative to the SM surface (with an error of uncertainty of p=0.001). In the oral section, the SK surface exhibited a 81% reduction in accumulated material relative to the SM surface (with an error of uncertainty of p=0.002).

Example 9

Figures 24A, 24B:
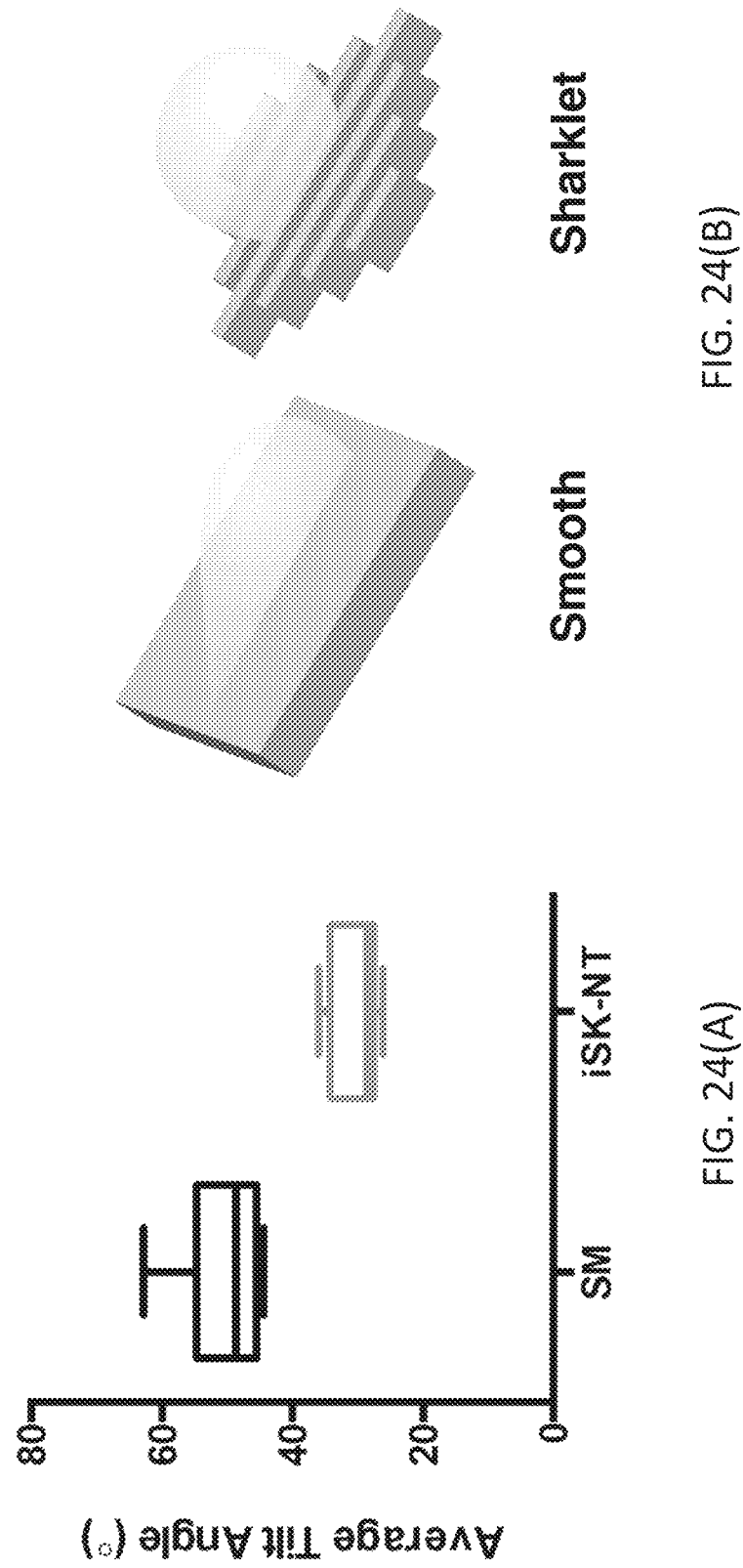
FIG. 24(A) shows the average tilt angle in degrees for a Smooth (SM) surface and a Sharklet (SK) patterned surface.
FIG. 24(B) shows an illustration of the tilt angle of a droplet of fluid on each of the Smooth (SM) and Sharklet (SK) patterned surfaces.

The following example was conducted to demonstrate the average tilt angle in degrees of artificial mucus on endotracheal tubes having a Smooth (SM) or a micropatterened (SK) surface disposed thereon. A goniometer was used to measure the tilt angle of a 10 µl droplet of artificial mucus flowing down each of the SM and SK surfaces, respectively. The results were plotted in a graph shown in FIG. 24(A). As may be seen from FIG. 24(A), the SK patterned surface demonstrated a significantly lower tilt angle than the SM surface. The SK surface allows flow capability of fluid at a lower tilt angle. Since clinical recommendations for endotracheal tubes indicate that the head of bed angle of the patient should be about 30 degrees, the SK surface allows flow to continue to occur through the tube. In contrast, the SM surface results in mucus pooling inside the tube, disrupting flow capacity therein. This difference in respective tilt angles for the SM and SK surfaces is illustrated in FIG. 24(B).

Example 10

Figures 25A, 25B:
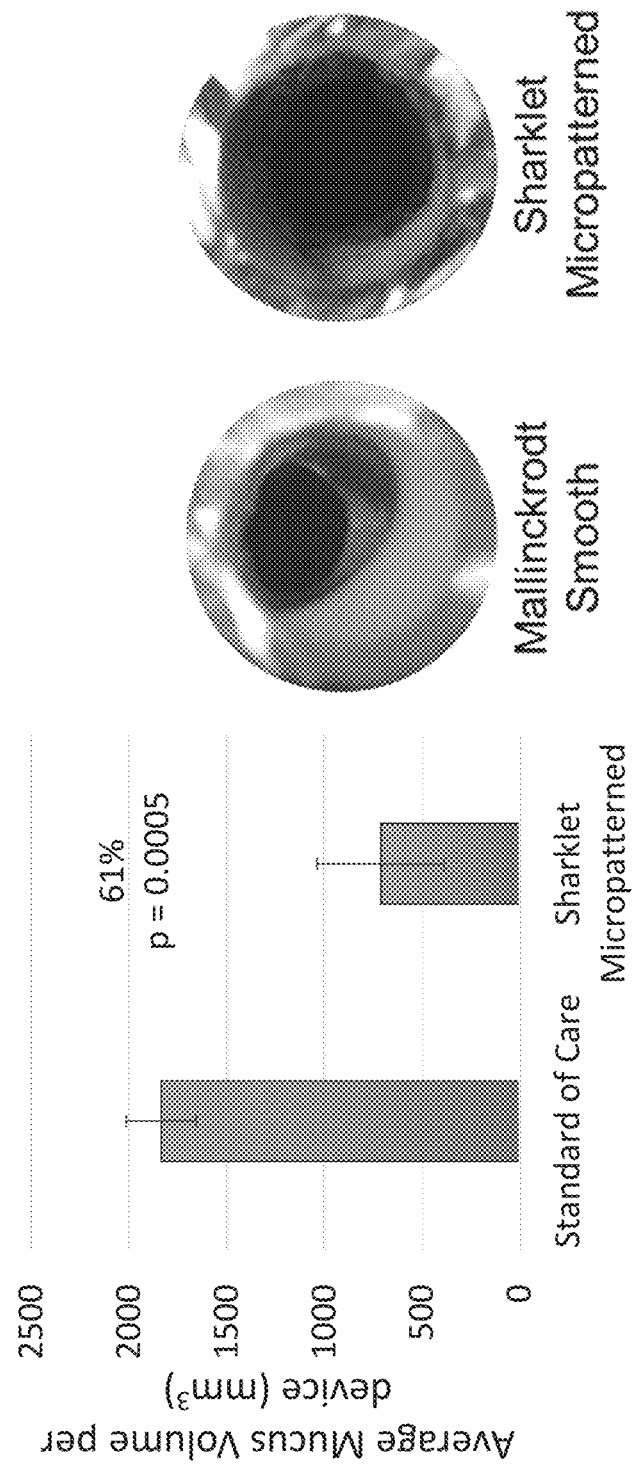
FIG. 25(A) shows the average mucus volume derived from ventilated sheep per endotracheal tube device for endotracheal tubes having a Smooth (SM) surface or a Sharklet (SK) patterned surface disposed thereon.
FIG. 25(B) shows photographs of the mucus accumulated in a cross-section of an endotracheal tube having a Smooth (SM) surface and in an endotracheal tube having a Sharklet (SK) patterned surface disposed thereon.

This example was conducted to demonstrate the average mucus volume per endotracheal tube device in $mm^3$ of mucus in endotracheal tubes used in Sheep. The endotracheal tubes had a Smooth (SM) or a micropatterened (SK) surface disposed thereon. The results were plotted in a graph shown in FIG. 25(A). As may be seen from FIG. 25(A), the SK patterned surface demonstrated about 61% lower average mucus per volume than the SM surface (with an error of uncertainty of p=0.0005). The relative amounts of accumulated mucus in a cross section of each of the endotracheal tubes having a SK or SM surface disposed thereon are shown in the photographs in FIG. 25(B).

Example 11

Figure 26:
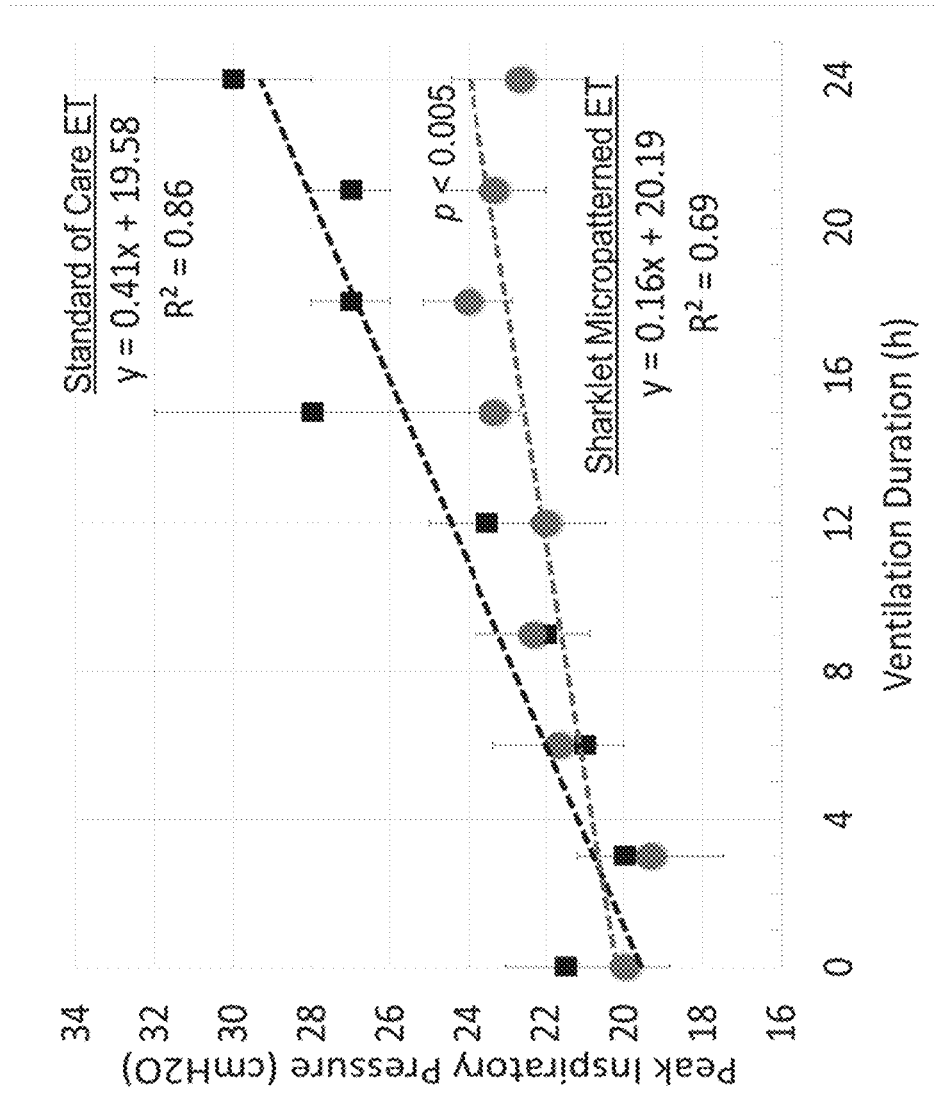
FIG. 26 shows the amount of pressure during ventilation of a group of sheep over 24 hours with an endotracheal tube having a Smooth (SM) surface and in an endotracheal tube having a Sharklet (SK) patterned surface disposed thereon.

This example was conducted to demonstrate the amount of pressure over time during mechanical ventilation using endotracheal tubes having a Smooth (SM) or a micropatterned (SK) surface disposed thereon. As mucus secretions accumulate inside of the endotracheal tubes, greater pressure is necessary to deliver a given volume of air. The peak inspiratory pressure in $cmH_2O$ was measured over a ventilation duration time in hours. The results were plotted in a graph shown in FIG. 26. As may be seen from FIG. 26, the SK patterned surface demonstrated that significantly lower pressure over time than the AM surface. In contrast, the rate of increase in pressure over time was significantly greater when a SM surface standard endotracheal tube was used in comparison to an endotracheal tube having the SK pattern disposed thereon.

While this disclosure describes exemplary embodiments, it will be understood by those skilled in the art that various changes can be made and equivalents can be substituted for elements thereof without departing from the scope of the disclosed embodiments. In addition, many modifications can be made to adapt a particular situation or material to the teachings of this disclosure without departing from the essential scope thereof. Therefore, it is intended that this disclosure not be limited to the particular embodiment disclosed as the best mode contemplated for carrying out this disclosure.

What is claimed is:

1. An article comprising:
    a first plurality of spaced features disposed on or in at least a portion of a surface of the article; the first plurality of spaced features arranged in a plurality of grouping; each grouping being a repeat unit of a plurality of repeat units that is repeated across the surface; the first plurality of spaced features within the grouping being spaced apart at an average distance of about 1 nanometer to about 500 micrometers to define a continuous path that traverses the first plurality of spaced features; where the continuous path extends across the portion of the surface of the article; each spaced feature having a surface that is substantially parallel to a surface on a neighboring spaced feature; each spaced feature being separated from the neighboring spaced feature; where the article comprises grids; wherein each grid encompasses the plurality of repeat units; and wherein the plurality of repeat units in adjacent grids are inclined at an angle of 50 to 150 degrees to each other.

2. The article of claim 1, where the continuous path is a linear path and is oriented parallel to a direction of fluid flow.

3. The article of claim 1, where the continuous path is a linear path and is oriented perpendicular to a direction of fluid flow.

4. The article of claim 1, where the continuous path is a linear path and is oriented at an angle of about 1 to about 50 degrees from a direction of fluid flow.

5. The article of claim 1, where the continuous path is a curvilinear path and is oriented at an angle of 0 to about 45 degrees from a direction of fluid flow.

6. The article of claim 1, where the continuous path is a curvilinear path and is oriented at an angle of about 60 degrees to about 90 degrees from a direction of fluid flow.

7. The article of claim 1, where the continuous path is defined by a plurality of linear channels.

8. The article of claim 1, where the first plurality of spaced features have thicknesses that vary with distance from a given point.

9. The article of claim 1, where the first plurality of spaced features have densities that vary with distance from a given point.

10. The article of claim 1, where the article is an endotracheal tube or a catheter, where the continuous path is a linear path and is oriented parallel to a direction of fluid flow and parallel to a longitudinal axis of the endotracheal tube or the catheter.

11. The article of claim 1, where the article comprises a plurality of sectors where the path is a linear path but is oriented differently in different sectors.

12. The article of claim 8, where the article is a wound dressing.

13. The article of claim 1, where the spaced features of the article are arranged in a zig zag fashion.

* * * * *